United States Patent
Frey et al.

(10) Patent No.: US 11,013,432 B2
(45) Date of Patent: May 25, 2021

(54) MEDICAL DEVICE FOR DETECTING AT LEAST ONE ANALYTE IN A BODY FLUID

(71) Applicant: Roche Diabetes Care, Inc., Indianapolis, IN (US)

(72) Inventors: Stephan-Michael Frey, Pfungstadt (DE); Oliver Kube, Worms (DE); Helmut Walter, Heppenheim (DE); Klaus Cornelius, Buerstadt (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 200 days.

(21) Appl. No.: 16/319,421

(22) PCT Filed: Aug. 3, 2017

(86) PCT No.: PCT/EP2017/069622
§ 371 (c)(1),
(2) Date: Jan. 21, 2019

(87) PCT Pub. No.: WO2018/024814
PCT Pub. Date: Feb. 8, 2018

(65) Prior Publication Data
US 2019/0231238 A1    Aug. 1, 2019

(30) Foreign Application Priority Data

Aug. 4, 2016 (EP) ..................................... 16182841

(51) Int. Cl.
*A61B 5/05* (2021.01)
*A61B 5/145* (2006.01)
(Continued)

(52) U.S. Cl.
CPC .......... *A61B 5/14532* (2013.01); *A61B 5/145* (2013.01); *A61B 5/14503* (2013.01);
(Continued)

(58) Field of Classification Search
CPC . A61B 5/14532; A61B 5/145; A61B 5/14503; A61B 5/14546; A61B 5/14865; A61B 5/15
See application file for complete search history.

(56) References Cited

U.S. PATENT DOCUMENTS

| 2006/0020189 A1* | 1/2006 | Brister ............... A61B 5/68335 600/345 |
| 2010/0331729 A1 | 12/2010 | Naito et al. |
| 2015/0073238 A1* | 3/2015 | Matsumoto ............ A61B 5/742 600/302 |

FOREIGN PATENT DOCUMENTS

| CN | 104168826 | 11/2014 |
| EP | 2253271 | 2/2012 |

(Continued)

*Primary Examiner* — Christian Jang
(74) *Attorney, Agent, or Firm* — Woodard, Emhardt, Henry, Reeves & Wagner, LLP

(57) ABSTRACT

A medical device (110) for detecting at least one analyte in a body fluid, a method of using a medical device (110) and a method for assembling a medical device are disclosed. The medical device (110) comprises:

at least one analyte sensor (122) having an insertable portion (160) adapted for at least partially being inserted into a body tissue (194) of a user, at least one electronics unit (172), wherein the analyte sensor (122) is operably connected to the electronics unit (172), wherein the electronics unit (172) comprises at least one interconnect device (174) with at least one electronic component attached thereto;

at least one insertion cannula (114), wherein the analyte sensor (122) partially is placed inside the insertion cannula (114);

wherein the insertion cannula (114) is movable in between at least one extended position (224) and at least one retracted position (222), wherein the electronics unit (172) remains in a fixed position (225) when the insertion cannula (114) is moved from the extended position (224) to the retracted position (222) or vice versa;

wherein the analyte sensor (122) comprises at least one active portion (148) having at least one sensor electrode (208) for sensing the analyte thereon;

(Continued)

wherein the analyte sensor (122) further comprises at least one passive portion (152) electrically connected to the electronics unit (172) in at least one connector portion (206);

wherein the passive portion (152) provides, in between the connector portion (206) and the active portion (148), at least one reserve loop (150) configured for compensating for an insertion path during movement from the retracted position (222) into the extended position (224) or vice versa.

14 Claims, 14 Drawing Sheets

(51) Int. Cl.
*A61B 5/1486* (2006.01)
*A61B 5/15* (2006.01)

(52) U.S. Cl.
CPC ...... *A61B 5/14546* (2013.01); *A61B 5/14865* (2013.01); *A61B 5/15* (2013.01)

(56) References Cited

FOREIGN PATENT DOCUMENTS

| | | |
|---|---|---|
| WO | WO 2007/123135 A1 | 11/2007 |
| WO | WO 2014/045448 | 3/2014 |

\* cited by examiner

MEDICAL DEVICE FOR DETECTING AT LEAST ONE ANALYTE IN A BODY FLUID

FIELD OF THE INVENTION

The invention relates to a medical device for detecting at least one analyte in a body fluid, a method of using a medical device and a method for assembling a medical device. The device and methods according to the present invention may mainly be used for long-term monitoring of an analyte concentration in a body fluid, such as for long-term monitoring of a blood glucose level or of the concentration of one or more other types of analytes in a body fluid. The invention may both be applied in the field of home care as well as in the field of professional care, such as in hospitals. Other applications are feasible.

RELATED ART

Monitoring certain body functions, more particularly monitoring one or more concentrations of certain analytes, plays an important role in the prevention and treatment of various diseases. Without restricting further possible applications, the invention will be described in the following text with reference to blood-glucose monitoring. However, additionally or alternatively, the invention can also be applied to other types of analytes.

Blood glucose monitoring, besides by using optical measurements, specifically may be performed by using electrochemical biosensors. Examples of electrochemical biosensors for measuring glucose, specifically in blood or other body fluids, are known from U.S. Pat. Nos. 5,413,690 A, 5,762,770 A, 5,798,031 A, 6,129,823 A or US 2005/0013731 A1.

In addition to so-called spot measurements, in which a sample of a bodily fluid is taken from a user in a targeted fashion and examined with respect to the analyte concentration, continuous measurements are increasingly becoming established. Thus, in the recent past, continuous measuring of glucose in the interstitial tissue (also referred to as continuous monitoring, CM) for example has been established as another important method for managing, monitoring and controlling a diabetes state.

In the process, the active sensor region is applied directly to the measurement site, which is typically arranged in the interstitial tissue, and, for example, converts glucose into electrical charge by using an enzyme (e.g. glucose oxidase, GOD), which charge is related to the glucose concentration and can be used as a measurement variable. Examples of such transcutaneous measurement systems are described in U.S. Pat. No. 6,360,888 B1 or in US 2008/0242962 A1.

Hence, current continuous monitoring systems typically are transcutaneous systems or subcutaneous systems, wherein both expressions, in the following, will be used equivalently. This means that the actual sensor or at least a measuring portion of the sensor is arranged under the skin of the user. However, an evaluation and control part of the system (also referred to as a patch) is generally situated outside of the body of the user, outside of the human or animal body. In the process, the sensor is generally applied using an insertion instrument, which is likewise described in U.S. Pat. No. 6,360,888 B1 in an exemplary fashion. Other types of insertion instruments are also known.

The sensor typically comprises a substrate, such as a flat substrate, onto which an electrically conductive pattern of electrodes, conductive traces and contact pads may be applied. In use, the conductive traces typically are isolated by using one or more electrically insulating materials. The electrically insulating material typically further also acts as a protection against humidity and other detrimental substances and, as an example, may comprise one or more cover layers such as resists.

US 2013/0313130 A1 discloses sensors having three-dimensional configurations that allow expansive 360°-sensing, i.e. sensing analyte from multiple directions, in the environments in which such sensors are disposed. Embodiments disclosed in this document provide analyte sensors having foldable substrates adapted to produce optimized configurations of electrode elements as well as methods for making and using such sensors. Typical embodiments of the invention include glucose sensors used in the management of diabetes.

WO 2013/013836 A1 discloses a one-time connection mechanism with an insertion element and a push-on element, with an integrated tamper-detection device for the one-time connection that can be created by the connection mechanism. The tamper-detection mechanism consists substantially of an electrical conductor section of a sensor loop, running at least in part in a connecting section between a head and a foot of the insertion element, and of a sensor monitoring device for the sensor loop, that is integrated into the insertion element or the push-on element. The sensor loop runs in certain sections in both the insertion element and the push-on element and is only electrically conductive if the one-time connection has been created. The one-time connection mechanism is especially suitable for earmarks for marking animals, but also for a mechatronic seal for electrically sealing closures or the like.

U.S. Pat. No. 8,696,600 B2 discloses a medical guide wire assembly comprising a guide wire having a proximal end and a distal end and at least one physiology parameter sensor. The proximal end of the guide-wire is provided with an elongated connector part, having connection electrodes, for insertion into a connector housing provided with an elongated tubing adapted to achieve electrical and mechanical connection to the elongated connector part. The connector housing is in its turn electrically or wirelessly connectable to a physiology monitor. The guide wire is provided with a core wire running essentially along the entire guide wire. A sensor signal processing circuitry is arranged in connection with the physiological sensor and is adapted to generate a processed sensor signal in response of a sensed parameter. The sensor signal processing circuitry comprises a modulation unit arranged to modulate the processed sensor signal and to generate a modulated sensor signal. The assembly comprises exactly two micro-cables that are connected to the sensor signal processing circuitry. The micro-cables run along the guide wire and are connected to the connection electrodes of the connector part. The core wire is actively used when transferring the processed and modulated sensor signal to the connector housing.

Despite the advantages implied by the above-mentioned known devices and methods, several technical challenges remain. Thus, in many continuous monitoring systems, the analyte sensor is separate from the electronics unit during insertion, and, subsequently, in electrical contact between the analyte sensor and the electronics unit has to be established. The electrical contact, however, in this case, typically has to be established by the user which in most cases does not have a medical training. Further, the electrical contact has to be sealed by using one or more sealing elements such as sealing lips or sealing rings. Thus, a significant technical challenge arises from the fact that these complex handling steps, typically performed by persons not having a medical training, have to be designed in a failsafe manner, in order to avoid technical malfunctions such as ingression of humidity into the analyte sensor system. Further, the mechanical tolerances for the sealing devices as well as the tolerances for electrical contacts are rather strict, which typically raises the production costs for the analytical systems. Additionally, typically, a large number of components are required which, in total, increase the volume of the system. In increased weight and volume, however, decreases the convenience of wearing for the user.

Problem to be Solved

It is therefore an objective of the present invention to provide a medical device for detecting at least one analyte in a body fluid, a method for using a medical device and a method for assembling a medical device, which at least partially avoid the shortcomings of known devices and methods of thus kind and which at least partially address the above-mentioned challenges. Specifically, devices and methods shall be disclosed which allow for easy manufacturing and simple handling processes by a user.

SUMMARY OF THE INVENTION

This problem is solved by a medical device for detecting at least one analyte in a body fluid, a method for using a medical device and a method for assembling a medical device with the features of the independent claims. Preferred embodiments, which might be realized in an isolated fashion or in any arbitrary combination are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the invention, a medical device for detecting at least one analyte in a body fluid is disclosed. The medical device comprises at least one analyte sensor having an insertable portion adapted for at least partially being inserted into a body tissue of a user. Further, the medical device comprises at least one electronics unit. The analyte sensor is operably connected to the electronics unit. The electronics unit comprises at least one interconnect device with at least one electronic component attached thereto. Further, the medical device comprises at least one insertion cannula. The analyte sensor is partially placed inside the insertion cannula. The insertion cannula is movable in between at least one extended position and at least one retracted position. The electronics unit remains in a fixed position when the insertion cannula is moved from the extended position to the retracted position or vice versa. The analyte sensor comprises at least one active portion having at least one sensor electrode for sensing the analyte thereon. The analyte sensor further comprises at least one passive portion electrically connected to the electronics unit in at least one connector portion. The passive portion in between the connector portion and the active portion, provides at least one reserve loop configured for compensating for an insertion path during movement from the retracted position into the extended position or vice versa. Thus, the passive portion or a part thereof may form the reserve portion.

As generally used within the present invention, the term "medical device" may refer to an arbitrary device configured for conducting at least one medical analysis and/or at least one medical procedure. The medical device therefore may generally be an arbitrary device configured for performing at least one diagnostic purpose and/or at least one therapeutic purpose. In the following, without restricting further embodiments, the present invention mainly will be described in terms of a medical device configured for performing at least one diagnostic purpose and, specifically a medical device comprising at least one analyte sensor for performing at least one analysis. The medical device may specifically comprise an assembly of two or more components capable of interacting with each other, such as in order to perform one or more diagnostic and/or therapeutic purposes, such as in order to perform the medical analysis and/or the medical procedure. Specifically, the two or more components may be capable of performing at least one detection of the at least one analyte in the body fluid and/or in order to contribute to the at least one detection of the at least one analyte in the body fluid. The medical device generally may be used for detecting at least one analyte in a body fluid of a user. Specifically, the medical device may be used for long-term monitoring or continuous monitoring of an analyte concentration in the body fluid of the user, such as in a body fluid contained in a body tissue of the user. The medical device generally may also be or may comprise at least one of a sensor assembly, a sensor system, a sensor kit or a sensor device.

As generally used within the present invention, the terms "patient" and "user" may refer to a human being or an animal, independent from the fact that the human being or animal, respectively, may be in a healthy condition or may suffer from one or more diseases. As an example, the patient or the user may be a human being or an animal suffering from diabetes. However, additionally or alternatively, the invention may be applied to other types of users or patients or diseases.

The term "body tissue" may generally refer to a cellular organizational level intermediate between cells and a complete origin. The body tissue may specifically be an ensemble of similar cells from the same origin that together carry out a specific function. Thereby, organs may then be formed by functional grouping together of multiple tissues. As an example for body tissue, interstitial tissue, i.e. connective tissue between cellular elements if a structure, may be named. As further used herein, the term "body fluid" generally may refer to a fluid which is typically present in a body or the body tissue of the user or the patient and/or which may be produced by the body of the user or the patient. Thus, as an example, the body fluid may be selected from the group consisting of blood and interstitial fluid. However, additionally or alternatively, one or more other types of body fluids may be used, such as saliva, tear fluid, urine or other body fluids.

As further used herein, the term "analyte" may refer to an arbitrary element, component or compound which may be present in the body fluid and the presence and/or the concentration of which may be of interest for the user, the patient or medical staff such as a medical doctor. Particularly, the analyte may be or may comprise an arbitrary chemical substance or chemical compound which may take part in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may be an analyte-specific detection.

As further used herein, the terms "sensor" and "analyte sensor" may generally refer to an arbitrary element which is adapted to perform a process of detection and/or which is adapted to be used in the process of detection. Thus, the sensor specifically may be adapted to determine the concentration of the analyte and/or a presence of the analyte. The terms "detection" and "detecting" generally refer to a process of determining a presence and/or a quantity and/or a concentration of the at least one analyte. Thus, the detection may be or may comprise a qualitative detection, simply determining the presence of the at least one analyte or the absence of the at least one analyte, and/or may be or may comprise a quantitative detection, which determines the quantity and/or the concentration of the at least one analyte. As a result of the detection, at least one signal may be produced which characterizes an outcome of the detection, such as at least one measurement signal. The at least one signal specifically may be or may comprise at least one electronic signal such as at least one voltage and/or at least one current. The at least one signal may be or may comprise at least one analogue signal and/or may be or may comprise at least one digital signal.

The analyte sensor specifically may be an electrochemical sensor. As used herein, an "electrochemical sensor" generally is a sensor which is configured to conduct an electrochemical measurement in order to detect the at least one analyte contained in the body fluid. The term "electrochemical measurement" refers to a detection of an electrochemically detectable property of the analyte, such as an electrochemical detection reaction. Thus, for example, the electrochemical detection reaction may be detected by comparing one or more electrode potentials. The electrochemical sensor specifically may be adapted to and/or may be usable to generate at least one electrical sensor signal which directly or indirectly indicates the presence and/or the extent of the electrochemical detection reaction, such as at least one current and/or at least one voltage. The detection may be analyte-specific. The measurement may be a qualitative and/or a quantitative measurement. Still, other embodiments are feasible. The analyte sensor may comprise at least two electrodes. The electrodes may comprise at least one working electrode. As used herein, the term "working electrode" refers to an electrode being adapted for or being usable for performing at least one electrochemical detection reaction for detecting the at least one analyte in the body fluid. The working electrode may have at least one test chemical being sensitive to the analyte to be detected. The term "test chemical" specifically may refer to an arbitrary material or a composition of materials adapted to change at least one detectable property in the presence of at least one analyte. This property may be an electrochemically detectable property. Specifically, the at least one test chemical may be a highly selective test chemical, which only changes the property if the analyte is present in the body fluid whereas no change occurs if the analyte is not present. The degree or change of the at least one property is dependent on the concentration of the analyte in the body fluid, in order to allow a quantitative detection of the analyte. As an example, the test chemical may comprise at least one enzyme, such as glucose oxidase and/or glucose dehydrogenase. The at least two electrodes may further comprise at least one counter electrode. As used herein, the term "counter electrode" refers to an electrode adapted for performing at least one electrochemical counter reaction and adapted for balancing a current flow required by the detection reaction at the working electrode. Additionally or alternatively the at least two electrodes may further comprise at least one reference electrode. The reference electrode may have a stable and well-known electrode potential. For potential materials usable for the counter electrode and/or the reference electrode, reference may be made to WO 2007/071562 A1 and/or the prior art documents disclosed therein. Other embodiments, however, are feasible.

The analyte sensor may further comprise at least one substrate. The at least two electrodes and/or at least two sensor contacts generally may be attached to the substrate. The sensor may further comprise at least two electrical traces which interconnect the electrodes and the sensor contacts and which may also be attached to the substrate. As used herein, the term "substrate" may generally refer to an arbitrary element which is suitable to carry one or more other elements disposed thereon or therein. As an example, the substrate may be a flat substrate, such as a substrate having a lateral extension exceeding its thickness by at least a factor of 2, at least a factor of 5, at least a factor of 10, or even at least a factor of 20 or more. The substrate specifically may have an elongated shape, such as a strip-shape and/or a bar-shape. The substrate, as an example, may comprise a shaft, specifically a shaft having an elongate shape. For example the shaft may have a shape selected from the group consisting of a strip, a needle, a tape. The analyte sensor, specifically the substrate, may at least to a large extend be made of at least one elastic material. Exemplarily, the analyte sensor may comprise polyimide. Specifically, the substrate may at least partially be made of at least one plastic material, specifically of at least one thermoplastic material, such as polyimide, particularly polyimide comprising at least one electrically conductive layer; polyethylene terephthalate. However, other thermoplastic materials may be feasible. Further, the substrate may comprise at least one layer of at least one electrically conductive layer such as a layer which comprises copper and/or gold. However, other embodiments are feasible.

The term "active portion" may generally refer to a portion of an arbitrary element which is configured for being involved in a process or a progress. Specifically, the active portion of the analyte sensor may be configured for detecting the analyte in the body fluid. Therefore, the active portion comprises the sensor electrodes for sensing the analyte. Thus, the active portion of the analyte sensor may comprise one or more working electrodes and one or more further electrodes, such as one or more counter electrodes and/or one or more reference electrodes. As an example, the active portion may comprise a section in between a tip of the analyte sensor which extends into the body tissue and a virtual line beyond the uppermost electrode of the analyte sensor, such that all electrodes of the analyte sensor are within said section. The virtual line, as an example, may be located, as an example, 1 mm or 2 mm above the last or uppermost electrode of the analyte sensor, such that the last or uppermost electrode of the analyte sensor still lies within said section.

Further, the term "passive portion" may generally refer to a portion of an arbitrary element which is configured for not being involved or not participating in a process or a progress. The passive portion, as an example, may comprise the whole analyte sensor, except for the active portion. Thus, as an example, the passive portion may comprise a section of the analyte sensor extending in between the virtual line defined above and an opposing end of the analyte sensor, opposing the above-mentioned tip extending into the body tissue. Specifically, the passive portion of the analyte sensor may be configured for transferring at least one signal, specifically at least one electronic signal to the electronics unit. Therefore, the passive portion may comprise electrical contacts. The electrical contacts may be electrically connected to the sensor electrodes via electrical traces. Further, the electrical contacts may be configured to be electrically connectable to an arbitrary electrical device. Specifically, the electrical contacts may be configured to be electrically connectable to the electronics unit. The active portion may correspond to or may be part of the insertable portion which will further be described below. The active portion may be located at one end of the analyte sensor and the passive portion may be located at one further end opposing the end of the analytes sensor. Further, the passive portion may comprise at least one section of the analyte sensor adjacent to the active portion.

As outlined above, the analyte sensor comprises the at least one connector portion. As used herein, the term "connector portion" may generally refer to a part of an arbitrary element which is configured to electrically connect components of the element to another element. Therefore, the connector portion may comprise electrical contacts being electrically connected to the electrodes of the analyte sensor via the electrical traces. The connector portion may be part of the passive portion of the analyte sensor or vice versa. The connector portion may comprise the electrical contacts as described above or as will further be described below.

As described above, the analyte sensor has an insertable portion adapted for at least partially being inserted into the body tissue of the user. As further used herein, the term "insertable portion" may generally refer to an arbitrary part of a whole object, suited for being inserted into a body tissue. For being suited into the body tissue, the insertable portion specifically may have appropriate dimensions and/or may contain one or more biocompatible surfaces. The insertable portion specifically may be part of the active portion defined above, or the active portion may be part of the insertable portion, or the insertable portion and the active portion may be identical. Specifically, the insertable portion may comprise 2% to 80% of the whole analyte sensor. Still, other embodiments may be feasible. Further, the term "inserting" may generally refer to an arbitrary process of introducing an object at least partially into another element. Thus, the object may be at least partially located under a surface of the other element. Further, the object may be at least partially surrounded by an interior of the other element. Therefore, the term "insertable" may refer to a property of the object of being at least partially introducible into another element. Specifically, the insertable portion of the analyte sensor may be configured for being inserted transcutaneously into the body tissue of the user. The active portion of the analyte sensor as described above or as will further be described below may be part of the insertable portion of the analyte sensor or vice versa. Further, the insertable portion may have a biocompatible surface as will further be described below.

The analyte sensor may further be a transcutaneous sensor. The term "transcutaneous" generally refers to a property of an arbitrary element of being adapted to be fully or at least partly arranged through an arbitrary body tissue of an human or animal being. In order to further render the element to be usable as a transcutaneous element, the element may fully or partially provide a biocompatible surface, i.e. a surface which, at least during durations of use, do not have any detrimental effects on the user, the patient or the body tissue. Further, the transcutaneous element generally may be dimensioned such that a transcutaneous insertion of the element into the body tissue is feasible, such as by providing a width in a direction perpendicular to an insertion direction of no more than 5 mm, preferably of no more than 2 mm, more preferably of no more than 1.5 mm. Thus, the term "subcutaneous" may generally refer to a property of an arbitrary element of being situated or lying under a skin and within the body tissue of the human or animal being. Specifically, the object may be configured to be introduced under the skin, exemplarily as an injection.

As outlined above, the passive portion forms, in between the connector portion and the active portion at least one reserve loop configured for compensating for an insertion path during movement form the retracted position into the extend position or vice versa. The term "loop" generally refers to an arbitrary element which has a non-straight shape, thereby interconnecting at least one first portion of the element with the at least one second portion of the element in a non-straight fashion.

Specifically, the loop may contain a first point and a second point being separated by a straight distance d1, wherein the first point and the second point are connected via a portion of the loop, wherein a distance d2 between the first point and the second point, measured along the loop or the portion of the loop, is at least 1.2 times d1, more preferably at least 2 times d1 and most preferably at least 3, at least 5 times or at least 10 times d1. Thereby, even though connected via the loop, the second point may move away from the first point, wherein the loop itself provides a reserve, as opposed to the situation in which the first point and the second point are connected by a straight element. The loop specifically may fully or partially be made of a flexible element. The loop in general may have a curved shape, with one or more curves, and/or may have a bent or folded shape, with one or more kinks or folds. The element may have an elongate shape and the curvatures may extend transverse to a direction of extension of the element. Thus, the curvatures may be present in one or more regions of the element, wherein the element may be straight in other regions. Thus, the reserve loop may comprise at least one folded section of the analyte sensor. As further used herein, the term "folded" may specifically refer to a property of an element, particularly of an elongate element, of being bended in at least one section. Thus, the element may comprise at least one first part and at least one second part which are separated from each other by a bended section. Exemplarily, the first part and the second part may be located parallel or at least almost parallel to each other. Specifically, the insertion cannula may comprise at least one major axis which extends along a direction of extension of the insertion cannula. The major axis may also be referred to as longitudinal axis. The folded section of the analyte sensor may be folded in a direction transverse to the major axis.

The term "reserve loop" may refer to an arbitrary element comprising at least one loop, wherein the loop is configured to provide or to keep in reserve parts of the element for a certain purpose. The reserve loop specifically may fully or partially be made of a flexible or deformable material. Specifically, the reserve loop may contribute to provide a desired length of the analyte sensor which is required for transcutaneously inserting the active portion of the analyte sensor into the body tissue. Thus, the reserve loop, as discussed above in the context of the term "loop", may contain a first point and a second point being separated by a straight distance d1, wherein the first point and the second point are connected via a portion of the reserve loop, wherein a distance d2 between the first point and the second point, measured along the reserve loop or the portion of the loop, is at least 1.2 times d1, more preferably at least 2 times d1 and most preferably at least 3 times, at least 5 times or at least 10 times d1. Thereby, even though connected via the reserve loop, the second point may move away from the first point, wherein the loop itself provides a reserve, as opposed to the situation in which the first point and the second point are connected by a straight element. The reserve loop specifically may be part of the passive portion and may fully or partially be made of a substrate or substrate material of the analyte sensor, specifically a flexible substrate portion which is one or more of bent, folded or kinked into a loop.

Thus, the reserve loop may be configured to be expanded or to be straightened during inserting the active portion of the analyte sensor into the body tissue. While the medical device is existent a state wherein the insertion cannula is in the retracted position and the analyte sensor is fully or at least to a large extend localized within the housing of the medical device, the analyte sensor may have the reserve loop. However, the reserve loop may be configured to be straightened fully or partially such that a degree of curvature is diminished. Further, in a state, wherein the insertion cannula is in a retracted position and the active portion of the analyte sensor is inserted into the body tissue, the reserve loop may be configured to stay within the straightened or enlarged state. Thus, the process of straightening the reserve loop may be an at least to a large extend a reversible process.

As outlined above, the reserve loop may be configured for compensating for an insertion path. As further used herein, the term "compensating" may refer to an arbitrary process of counterbalancing another process. As described above, the insertion cannula is moveable from the retracted position into the extended position or vice versa. Thereby, one part of the analyte sensor, specifically at least the connector portion, may be configured to stay fixedly positioned, while a further part of the analyte sensor, specifically at least the insertable portion and/or a tip of the analyte sensor, may be configured to be moveable from an interior of the medical device to an outer region of the medical device. Thus, while the first portion and the second portion may be separated during the insertion process by a distance Δd, the reserve loop may provide a reserve which counterbalances this distance, i.e. provides at least the reserve, such as a tape or substrate reserve, having a length of Δd. Therefore, the analyte sensor may require to have a section which may specifically be stored within the interior of the medical device and which is configured to counterbalance the movement of the further part of the analyte sensor as described above. Thus, the term "path" may generally refer to an arbitrary distance an element needs to cover for a certain purpose. Specifically, the term "insertion path" may refer to a distance the analyte sensor needs to cover from an interior of the medical device into the body tissue.

The analyte sensor may be stored in a first shape configuration when the insertion cannula is in the retracted position, wherein the analyte sensor is configured to be transformable into a second shape configuration when the insertion cannula is in the extended position. As further used herein, the terms "first shape configuration" and "second shape configuration" may refer to two different states or shapes in which an arbitrary element may be existent and be reversibly transformable. The terms "first shape configuration" and "second shape configuration" may be considered as nomenclature only, without numbering or ranking the named elements, without specifying an order and without excluding a possibility that several kinds of first shape configurations and second shape configuration may be present. Further, additional shape configurations such as one or more third shape configurations may be present.

The reserve loop may be configured to be formed or magnified when the insertion cannula is in the retracted position, wherein the reserve loop is configured to be completely or at least to a large extend diminished when the insertion cannula is in the extended position. Alternatively, the reserve loop may be formed when the insertion cannula is in the extended position, wherein the reserve loop is configured to be completely or at least to a large extend diminished when the insertion cannula is in the retracted position. As further used herein, the term "magnifying" may refer to a process wherein a radius of the reserve loop is increased. Further, the term "magnifying" may refer to a process wherein a portion of the analyte sensor, which contributes to the reserve loop is increased. On the contrary, the term "diminishing" may refer to a process wherein the radius of the reserve loop is decreased or wherein the reserve loop is even completely offset such that the respective section of the analyte sensor is at least to a large extend existent in a straight shape. Further, the term "diminishing" may refer to a process wherein a portion of the analyte sensor, which contributes to the reserve loop is decreased. Further, the term "forming" may refer to a process wherein in a first state, no reserve loop is existent and wherein the reserve loop is generated during the process.

As further used herein, the term "radius" of the reserve loop may refer to a dimension between an imaginary center of the reserve loop to a circumference of the reserve loop. However, the reserve loop does not necessarily have a circular shape. Thus, the term radius may refer to an averaged dimension between the imaginary center to different positons of the circumference of the reserve loop. Exemplarily, the reserve loop may have a basic shape selected from the group consisting of: a circular shape, an elliptical shape, an oval shape, a meandering shape, a curved shape, a bent shape, a kinked shape, a folded shape, a leporello fold shape, a spiral shape. Further, the reserve loop may have an elastic element such as an elastic section. However, other embodiments may be feasible. However, other basic shapes may be feasible. As further used herein, the term "basic shape" may refer to a shape of an object, wherein the object may have an appearance which resembles with regard to an overall impression a primary form such as a circle or an oval. However, deviations may be feasible. Exemplarily, the basic shape may correspond to a half circle and the half circle may have slight deviations from a perfect half circle. However, other embodiments may be feasible. Exemplarily, the reserve loop may have a radius of less than 10 mm, preferably of less than 5 mm, more preferably of less than 2 mm. Specifically, the analyte sensor may be configured such that during such a bending, the substrate as well the electrical contacts, the sensor electrodes, the electrical traces and further components of the analyte sensor may be stable and may not or at least to a large extend be damaged.

As further used herein, the term "insertion cannula" may refer to an arbitrary element which may be insertable at least partially into an arbitrary body tissue, particularly in order to deliver or to transfer a further element. The insertion cannula may at least partially be made of at least one biocompatible material. Further, the insertion cannula may specifically be or may comprise a hollow tube or a hollow needle. As described above, the insertion cannula has a lumen which is fully or partially enclosed by a wall of the insertion cannula. The term "lumen" generally refers to an interior volume of an arbitrary element. The interior volume may specifically be an open interior volume. Thus, the interior volume may not be fully enclosed or surrounded by a wall of the element. Instead, a flow of a fluid medium or an insertion of another object from one end of the element to a further end through the lumen may be feasible. As further used herein, the term "wall" may generally refer to an arbitrary structure, specifically a structural material, which is configured to at least partially surround another object or volume thereby defining physical limits of an object. Further, the wall may be configured to protect the volume or the other object at least partially enclosed by the wall.

The insertion cannula may comprise at least one insertion cannula slider. The term "slider", also referred to as a "slide", generally refers to an element which is guided in a slidable fashion, such as by one or more slide rails or slide guides. The insertion cannula slider may be fixedly attached to the insertion cannula. Further, the insertion cannula slider may be guided in a slidable fashion in such a way that the insertion cannula slider moves towards the body tissue and transfers at least parts of the analyte sensor, specifically the insertable portion of the analyte sensor, into the body tissue. The insertion cannula slider may be configured to insert the insertion cannula at least partially into the body tissue. Thereby m The insertion cannula, when being in the extend position, may have an angle of 30° to 60°, preferably of 40° to 50°, more preferably of 45°, to a bottom side of the medical device. Further, the insertion cannula slider may be configured to retract the insertion cannula into the interior of medical device after insertion with the insertable portion of the analyte sensor remaining within the body tissue. Thus, the insertion cannula may be configured such that the insertion cannula is withdrawn into the medical device after insertion of the analyte sensor.

Specifically, the insertion cannula may have a shape which corresponds to a shape of the analyte sensor. Exemplarily, the analyte sensor may have a rectangular shape such as a rectangular cross-section perpendicular to a longitudinal axis of the analyte sensor and the insertion cannula may have a rectangular shape such as a rectangular cross-section perpendicular to a longitudinal axis of the insertion cannula, too. Thereby, the term "rectangular cross-section" may refer to a cross-section wherein the cross-section comprises two longitudinal sides and two narrow sides. The sides may be perpendicular to each other and the longitudinal sides may have a larger length than the narrow sides, respectively. However, small deviations may be feasible. The insertion cannula may be selected from the group consisting of: a closed cannula with the wall circumferentially enclosing a lumen of the insertion cannula; a slotted cannula, with the insertion cannula having a slot extending in an axial direction. Thereby, the term "axial direction" may refer to a direction situated in or on an axis of the insertion cannula. Specifically, the term axis direction may refer to a direction parallel to the longitudinal axis of the insertion cannula.

One part of the analyte sensor, particularly the insertable portion of the analyte sensor, may be received in the insertion cannula and one further part of the analyte sensor may be located outside of the insertion cannula, specifically when the insertion cannula is in the retracted position. Exemplarily, the insertion cannula may be a slotted cannula and the slot may extend in the longitudinal axis of the insertion cannula. Specifically, the slot may be located on one of the longitudinal sides of the rectangular cross-section of the insertion cannula. Thereby, the analyte sensor may have a straight shaft and at least the insertable portion of the analyte sensor may be received in the insertion cannula. Specifically, the part of the analyte sensor which his received in the insertion cannula may have a cross-section parallel to the longitudinal axis of the analyte sensor which alters along the longitudinal axis of the analyte sensor. Specifically, the analyte sensor may have narrower sections.

Alternatively, the analyte sensor may be folded such that the further part of the analyte sensor is adjacent to the insertion cannula, particularly adjacent to the longitudinal axis of the insertion cannula. Specifically, the shaft of the analyte sensor may be folded. Specifically, the analyte sensor may be folded such that the analyte sensor is at least to a large extend situated in a plane based on the longitudinal axis of the analyte sensor and not on an axis perpendicular to the longitudinal axis of the analyte sensor. The folded analyte sensor as described above may be at least partially received in a slotted cannula, wherein the slot may extend in the longitudinal axis of the insertion cannula. Further, the slot may be located on one of the narrow sides of the rectangular cross-section of the insertion cannula. Thereby, the part of the analyte sensor, specifically at least the insertable portion of the analyte sensor may be received in the insertion cannula and the further part of the analyte sensor is located adjacent to the insertion cannula. This may specifically be advantageous as only small tolerance specifications may be required with regard to a relation of dimensions of the analyte sensor and dimension of the insertion cannula.

The medical device may comprise at least one analyte sensor slider. Specifically, the analyte sensor slider may be configured to be movable within the medical device when the insertion cannula is moved from the retracted position in the extended position. Exemplarily, the analyte sensor slider may be configured to be pressed towards the body tissue via the insertion cannula slider as described above or as will further be described below. The analyte sensor slider may be configured to stay within the medical device after inserting the insertable portion of the analyte sensor within the body tissue and after removing the insertion cannula from the medical device as will further be described below. Thus, the analyte sensor slider may serve as a sealing element. The term "sealed" may generally refer to a property of an arbitrary element of being completely or at least to a large extent isolated from a surrounding environment. The term "sealing element" may generally refer to an arbitrary element which is configured to cover one or more elements to be sealed off from environmental influences. Further, the slider may comprise at least one receptacle. The receptacle may be configured to receive the reserve loop at least partially when the insertion cannula is in the retracted position. Specifically, the receptacle may be configured to give the reserve loop mechanical stability when the insertable portion is received in the body tissue.

As further used herein, the terms "extended position" and "retracted position" may refer to two different positions, states or configurations in which an element may be existent and may be reversibly transferable. However, the terms "extended position" and "retracted position" may be considered as nomenclature only, without numbering or ranking the named positions, without specifying an order and without excluding a possibility that several kinds of extended positions and several kinds of retracted positions may be present. Further, additional positions may be present. Specifically, the term "extended position" may refer to a state, wherein the insertion cannula at least partially protrudes from the medical device. Further, the term extended position may refer to a state, wherein the insertion cannula is at least partially inserted into the body tissue of the user or the patient. The term "retracted position" may refer to a state, wherein the insertion cannula is fully or at least to a large extend located within an interior of the medical device.

As used herein, the term "electronics unit" generally refers to an arbitrary device having at least one electronic component. The electronics unit may comprise at least one measurement device configured for performing an electrochemical measurement with the analyte sensor. Specifically, the electronics unit may comprise at least one electronic component for one or more of performing a voltage measurement, performing a current measurement, recording sensor signals, storing measurement signals or measurement data, transmitting sensor signals or measurement data to another device. Further, the electronic component may comprise an application-specific integrated circuit. The electronics unit may specifically be embodied as a transmitter or may comprise a transmitter, for transmitting data. Other embodiments of the electronic components are feasible.

Further, as outlined above, the analyte sensor is "operably connected" to the electronics unit. The term "operably connected" may specifically refer to a state, wherein two or more objects are connected to each other such that they can interact with each other. Specifically, the analyte sensor may be operably connected to the electronics unit such that sensor signals of the analyte sensor may be transmitted to the electronics unit. Specifically, the analyte sensor may be operably connected to the electronics unit via the electrical contacts of the analyte sensor as described above or as will further be described below.

As outlined above, the electronics unit comprises the at least one interconnect device. As used herein, an "interconnect device" generally refers to an element or a combination of elements which are capable of carrying one or more electronics components and interconnecting these one or more electronics components, such as interconnecting the one or more electronics components electrically or electronically with each other and/or with one or more contact pads. As an example, the interconnect device may comprise a base and one or more electrical traces and/or one or more electrical contact pads disposed thereon and/or therein. As an example, the interconnect device may comprise a printed circuit board which may either be rigid or fully or partially be embodied as a flexible printed circuit board. The base, as an example, may be a flat element having a lateral extension which exceeds its width by at least a factor of 10, more preferably by at least a factor of 100 or even a factor of 1000. Other embodiments are feasible. Rigid materials which may be used for the base are fiber-enforced plastic materials such as fiber-enforced epoxy materials like glass-fiber-enforced epoxy materials such as FR-4. Other materials may be used. Specifically, as outlined above, the base may be a flexible base, such that the interconnecting device may fully or partially be embodied as a flexible printed circuit board. In this case, as an example, the flexible base may fully or partially be made of one or more flexible plastic materials such as one or more plastic foils or laminate, such as polyimides.

As outlined above, the interconnect device comprises the at least one electronic component attached thereto. As an example, the electronic component may directly be attached to the interconnect device by using one or more of soldering, bonding or electrically conductive adhesive. Thus, the interconnect device may comprise one or more contact pads, wherein corresponding contacts of the electronic component are electrically connected to the one or more contact pads. Additionally or alternatively, however, the at least one electronic component may indirectly be attached to the interconnect device, such as via at least one electronic housing. Thus, the at least one electronic housing may be attached to the interconnect device. Still, an electrical contact between the at least one electronic component and the interconnect device may be made, such as via at least one contact passing through the electronic housing. The electronic housing may fully or partially surround the at least one electronic component.

Further, as outlined above, the electronics unit remains in a fixed position when the insertion cannula is moved from the extend position to the retracted position or vice versa. As further used herein, the term "fixed position" refers to a state of an arbitrary element of not being moved or at least to a large extend not being moving during a certain action or progress. Thus, the element may stay a firm at a certain position during the action or the progress.

The medical device may further comprise at least one housing. As generally used herein, the term "housing" may refer to an arbitrary element which is adapted to fully or partially surround and/or receive one or more elements in order to provide one or more of a mechanical protection, a mechanical stability, an environmental protection against moisture and/or ambient atmosphere, a shielding against electromagnetic influences or the like. Thus, the housing may simply provide a basis for attachment and/or holding one or more further components or elements. Additionally or alternatively, the housing may provide one or more interior spaces for receiving one or more further components or elements.

The housing may comprise at least one insertion cannula compartment and at least one electronics unit compartment. As used herein, the term "compartment" may generally refer to an arbitrary subpart of a superior element creating a partially or fully enclosed space that may be usable to contain and/or store objects. The subpart may specifically be completely or at least to a large extend closed such that an interior of the compartment may be isolated from a surrounding environment. Exemplarily, the compartment may be separated from other parts of the superior element by one or more walls. Thus, within the housing, two or more compartments may be comprised which may fully or partially be separated from one another by one or more walls of the housing. Each compartment may comprise a continuous space or lumen configured for receiving one or more objects. The housing, however, may also fully or partially be embodied by using one or more deformable materials, in a deformable state and/or in a hardened or a cured state. Specifically, the insertion cannula compartment may be configured to host the insertion cannula and the analyte sensor, specifically the active portion of the analyte sensor, at least to a large extend, respectively. Further, specifically, the electronics unit compartment may be configured to host the electronics unit at least to a large extend and parts of the analyte sensor, specifically the connector portion of the analyte sensor.

The insertion cannula compartment may form a sealed compartment. The term "sealed compartment" may refer to a property of a compartment of being isolated from a surrounding environment such that a transfer of gas, fluids and/or solid elements is completely or at least to a large extent reduced. Specifically, the insertion cannula compartment may be configured to provide a sterile compartment for the insertable portion of the analyte sensor. The term "sterile" may generally refer to a property of an arbitrary object of being at least to a large extent free from all forms of life and/or other biological agents such as prions, viruses, fungi, bacteria or spore forms. Thus, the sterile object may be treated by at least one sterilization process that eliminates and/or deactivates the forms of life and/or the other biological agents. The sterilization process may comprise one or more of the following techniques: heating, chemical treatment, irradiation, high pressure, filtration. However, other techniques are feasible. The sterilization process may be conducted within a specified region or area of the object such as a surface of the object.

Exemplarily, the insertion cannula compartment may comprise at least one detachable cap. The insertion cannula may be received in the detachable cap after insertion of the analyte sensor and the detachable cap may be configured to be detachable from the medical device after insertion of the analyte sensor. The term "cap" may refer to an arbitrary element which is configured to close or to seal a volume. Specifically, the cap may close or seal an opening of an arbitrary container. The term "detachable" may refer to a property of an element of being removable from an arbitrary object. Thereby, a close bonding or contact between the element and the object may be disconnected. Generally, the element may be removable in a reversible manner wherein the element may be attachable and detachable from the object or in an irreversible manner wherein the element may not be attachable to the object after detachment. The detachable cap may exemplarily be connected to the insertion cannula compartment via at least one screwing connection or via at least one form-locked connection or via at least one frictional connection. However, other embodiments may be feasible.

The insertion cannula compartment may comprise at least one opening, particularly at least one passage opening. Thereby, the insertion cannula may be movable from the insertion cannula compartment into the body tissue or vice versa. The opening may specifically have a shape that corresponds to a shape of the insertion cannula. Further, the opening may be covered via at least one sealing element providing a sterile packaging of the insertion cannula compartment.

The insertion cannula compartment and the electronics unit compartment may be separated by at least one separating wall. The term "separating wall" may refer to an arbitrary wall which is configured to divide two or more different areas. The separating wall may comprise at least one analyte sensor receptacle. The analyte sensor may be partially received in the insertion cannula compartment and partially received in the electronics unit compartment.

A section of the analyte sensor may be received in the analyte sensor receptacle. Thus, the section of the analyte sensor receptacle may be received in the analyte sensor receptacle such that at least the connector portion of the analyte sensor is located in the electronics unit compartment and such that at least the insertable portion of the analyte sensor is located in the insertion cannula compartment. The analyte sensor receptacle, specifically the analyte sensor receptacle with the section of the analyte sensor received therein, may be tightly sealed form a surrounding environment by at least one of an adhesive; a sealing element, particularly a sealing element made of at least one thermoplastic elastomer; a heat-sealing; a screw connection; grouting. However, other embodiments may be feasible. Specifically, the analyte sensor receptacle may be sealed from the insertion cannula compartment and from the electronics unit compartment, respectively. The adhesive may exemplarily be or comprise at least one glue which may be configured to be applied in a fluid form to the analyte sensor receptacle and to harden afterwards.

Further, the housing may comprise at least one adhesive element configured for attaching the medical device to the skin site of the user or the patient. The adhesive element may specifically be a flat element and may have at least one adhesive surface. Exemplarily, the adhesive element may be a plaster. The adhesive element may be fixedly attached to a bottom side of the housing and the adhesive surface may be configured to face the skin side of the user or the patient.

In a further aspect of the present invention, a method of using a medical device and a method for assembling a medical device are disclosed. The methods comprise the method steps as given in the independent claims and as listed as follows. The method steps may be performed in the given order. However, other orders of the method steps are feasible. Further, one or more of the method steps may be performed in parallel and/or on a timely overlapping fashion. Further, one or more of the method steps may be performed repeatedly. Further, additional method steps may be present which are not listed.

The method of using a medical device comprises using the medical device as described above and as will further be described below. Further, the method of using a medical device comprises the following steps:
 i. placing the medical device onto a skin site of the user, with the insertion cannula being in the retracted position;
 ii. extending the insertion cannula into the extended position, whereby a shape of the reserve loop is altered as the active portion advances into the body tissue; and
 iii. retracting the insertion cannula into the retracted position, with the active portion remaining in the body tissue.

Before usage, the medical device may be provided as a sterile packaging. The sealing film as described above may be removed from the bottom side of the medical device, specifically from the cover element, exposing the opening of the insertion cannula compartment, the insertion cannula and the insertable portion of the analyte sensor.

The step of placing the medical device onto the skin site of the user may comprise placing the medical device onto the skin site via the at least one adhesive element such as the plaster. The adhesive element may be fixedly attached to the bottom side of the electronics unit. Further, the adhesive element may comprise the at least one adhesive surface facing the skin site of the user or the patient.

The step of extending the insertion cannula into the extended position may be conducted via an insertion aid. The term "insertion aid" may generally refer to an arbitrary device which is configured to support an insertion of an arbitrary element at least partially into another object. Thereby, the insertion aid itself may not be inserted into the other object. Exemplarily, the insertion aid may have an insertion aid receptacle. The insertion aid receptacle may have a shape which corresponds to the insertion cannula compartment of the housing of the medical device hosting the insertion cannula and the analyte sensor at least partially. Thus, the insertion aid may be mountable to the medical device through enclosing the insertion cannula compartment of the medical device via the insertion aid receptacle at least partially. The insertion aid may have a button which may be pressable by the user or the patient. The button may be configured to trigger an insertion mechanism thereby extending the insertion cannula into the extended position. Specifically, by pressing the button the insertion cannula may be pressed towards the skin site of the user via the insertion cannula slider. The term "insertion mechanism" may generally refer to an assembly of components which are configured to interact with each other with the purpose of inserting an element at least partially into another object. Therefore, the insertion mechanism may be configured such that a movement of the element in a direction of insertion, i.e. toward a surface of the other object is introduced.

As further used herein, the term "altering of a shape" refers to an arbitrary process wherein a form or a configuration of an object becomes different or modified. The process may be triggered by an external force, specifically by an external mechanical force. The altering may specifically refer to a reversible process, e.g. the object may be transferable to its original form without any or at least only with minor damages of the object. The term "diminishing a loop" may refer to an arbitrary process of reducing a portion of an arbitrary object, specifically of an elongate object, which contributes to a looped section or to a curved section of the object. Thereby, the loop may be reduced, e.g. a radius of the loop may be reduced. On the contrary, the term "magnifying a loop" may refer to an arbitrary process of increasing a portion of an arbitrary object, specifically of an elongate object, which contributes to a looped section or to a curved section of the object. Thereby, the loop may be increased, e.g. a radius of the loop may be increased. Further, the term "forming of loop" may refer to an arbitrary process, wherein, in a first configuration, an arbitrary object, specifically an elongate object, may be in a straight shape and may be at least to a large extend free from curves. Thereby, in a second configuration, at least a section of the object may be altered such that the section may have a curved shape.

The retracting of the insertion cannula into the retracted position may exemplarily be supported by a return spring. The term "return spring" may generally refer to an arbitrary elastic objects which is used to store mechanical energy. In case an object may be coupled to the return spring, the return spring may be configured to be tensioned when the object is moved. Thereby, the return spring may be configured to move the object back to its original position when the return spring is relaxed. Specifically, the return spring may be configured to be tensioned during insertion of the insertable element into the body tissue. Further, the return spring may be configured to support a withdrawing of the insertion cannula from the body tissue after insertion. Still other embodiments for supporting a retracting of the insertion cannula into the retracted position are feasible.

After retracting the insertion cannula into the retracted position, with the active portion remaining in the body tissue at least parts of the insertion cannula compartment may be removed from the medical device. The part may specifically comprise the insertion cannula. Thus, the insertion cannula may be removed by removing the part of the insertion cannula. The part of the insertion cannula may specifically correspond to the detachable cap as described above or as will further be described above. The detachable cap may exemplarily be attached to the housing of the medical device by means of a tight fit or friction securing. The tight fit or friction securing may be disconnected by the user, specifically by applying a mechanical force by the user.

The opening of the insertion cannula compartment as well as the insertable portion of the analyte sensor may be shielded from external influences via the analyte sensor slider as described above or as will further be described below. The analyte sensor slider may exemplarily be fixedly attached to the housing of the medical device by at least one snap element such as by at least one kick-over spring. However, other embodiments may be feasible. Thus, the analyte sensor slider may seal the opening of the insertion cannula compartment. However, the sealing does not necessarily need to be a gas-tight sealing. A transfer of fluidic media such as gas and/or fluids between an exterior of the medical device and an interior of the medical device formed by the analyte sensor slider, the cover element and a part of the skin site exposed by the opening of the insertion cannula compartment may be allowable.

After removing the insertion cannula compartment, the medical device may optionally be covered by a protective element. The term "protective element" may refer to an arbitrary element which is adapted to fully or at least partially surround and/or receive one ore more elements in order to provide a mechanical protection. Specifically, the protective element may be configured to cover the analyte sensor slider of the medical device as described above. The protective element may be made of a rigid material such as a rigid plastic material. Further, the protective element may be configured to be fixedly attachable to medical device, specifically to the housing of the medical device such as by a snap connection. Still, other embodiments are feasible.

The method for assembling a medical device as described above or as will further be described below comprises the following steps:

a. providing a housing of the medical device, the housing comprising at least one insertion cannula compartment and at least one electronics unit compartment;

b. placing the analyte sensor into the housing, wherein the active portion and the reserve loop are at least partially placed in the insertion cannula compartment and the connector portion is at least partially placed in the electronics unit compartment;

c. sterilizing the insertion cannula compartment; and d. electrically connecting the electronics unit to the passive portion of the analyte sensor.

Exemplarily, the housing may be manufactured by injection molding. The electronics unit compartment and the insertion cannula compartment may be manufactured as one piece. Alternatively, at least parts of the insertion cannula compartment, specifically the detachable cap, may be manufactured as one or more separate pieces. Before or after conducting step b) at least one further element may be placed at least partially into the insertion cannula compartment. The at least one further element may be selected from the group consisting of: the insertion cannula; the analyte sensor slider.

The term "sterilizing" may refer to an arbitrary process of receiving at least to a large extend a sterile object. Step c) may be conducted by at least one sterilization process based on radiation. Specifically, the sterilization process may be based on radiation. Exemplarily, the sterilization process may be based on at least one of e-beam sterilization, gamma sterilization or Xray sterilization. However, other embodiments may be feasible. The method may further comprise at least one step of sterilizing the electronics unit, particularly by gas sterilization such as by using ethylene oxide. Specifically, the method may be performed such that step c) is performed before performing step d), in order to avoid exposing the electronics unit to the radiation. The electronics unit compartment does not necessarily need to be sterilized or sealed from a surrounding environment.

The proposed medical device, the method for assembling a medical device and the method of using a medical device provide many advantages over known devices and methods.

Usually, in common medical devices the user electrically contacts the electronics unit to the electrical contacts of the analyte sensor and seals the electrical contacts after inserting the analyte sensor. Therefore, common medical devices usually comprise sealing elements such as sealing rings and/or sealing lips. Further, common medical devices usually comprise contact elements such as contact pins or conductive rubbers for electrically contacting the electronics unit to the electrical contacts of the analyte sensor. Consequently, by applying common medical devices by the user or by the patient application errors may occur. Exemplarily, the user or the patient may not successfully tighten the medical device. Further, the sealing elements such as the sealing rings or the sealing lips may usually require high tolerance specifications. This may generally lead to high inspection costs. Moreover, the electronically contacting of the analyte sensor and the electronics unit may usually require high tolerance specifications such as concerning surface conditions, contact resistances, geometries and/or contact forces, too. Thus, this may also generally lead to high inspection costs. Further, common medical devices may usually require a large number of components. This may lead to a reduced wearing comfort for the user or the patient.

Therefore, the passive portion of the analyte sensor of the medical device according to the present invention may be elongated such that there is a thigh, electrical connection of the analyte sensor to the electronic unit and to the energy supply. The connection between the analyte sensor and the electronics unit may specifically be inseparable. Further, the connection may be testable during assembling the medical device. Beyond, no sensor connector may be required. Thus, only a small construction volume may be required. Further, a number of application errors may be diminished at least to a large extend. Moreover, the medical device according to the present invention may have a robust design.

Summarizing the findings of the present invention, the following embodiments are preferred:

Embodiment 1

A medical device for detecting at least one analyte in a body fluid, the medical device comprising:
- at least one analyte sensor having an insertable portion adapted for at least partially being inserted into a body tissue of a user,
- at least one electronics unit, wherein the analyte sensor is operably connected to the electronics unit, wherein the electronics unit comprises at least one interconnect device with at least one electronic component attached thereto;
- at least one insertion cannula, wherein the analyte sensor partially is placed inside the insertion cannula;
- wherein the insertion cannula is movable in between at least one extended position and at least one retracted position, wherein the electronics unit remains in a fixed position when the insertion cannula is moved from the extended position to the retracted position or vice a versa;
- wherein the analyte sensor comprises at least one active portion having at least one sensor electrode for sensing the analyte thereon;
- wherein the analyte sensor further comprises at least one passive portion electrically connected to the electronics unit in at least one connector portion;
- wherein the passive portion provides, in between the connector portion and the active portion, at least one reserve loop configured for compensating for an insertion path during movement from the retracted position into the extended position or vice versa.

Embodiment 2

The medical device according to the preceding embodiment, wherein the reserve loop comprises at least one folded section of the analyte sensor.

Embodiment 3

The medical device according to the preceding embodiment, wherein the insertion cannula comprises at least one major axis which extends along a direction of extension of the insertion cannula, wherein the folded section of the analyte sensor is folded in a direction transverse to the major axis.

Embodiment 4

The medical device according to any one of the preceding embodiments, wherein the reserve loop has a radius of less than 10 mm, preferably of less than 5 mm, more preferably of less than 2 mm.

Embodiment 5

The medical device according to any one of the preceding claims, wherein the reserve loop has a basic shape that corresponds at least partially to a form selected from the group consisting of: a circular shape; an oval shape; an elliptical shape; a meandering shape, a curved shape, a bent shape, a kinked shape, a folded shape, a leporello fold shape, a spiral shape.

Embodiment 6

The medical device according to any one of the preceding embodiments, wherein the analyte sensor is stored in a first shape configuration when the insertion cannula is in the retracted position, wherein the analyte sensor is configured to be transformable into a second shape configuration when the insertion cannula is in the extended position.

Embodiment 7

The medical device according to any one of the preceding embodiments, wherein the reserve loop is formed according to one of the following options:
the reserve loop is formed or magnified when the insertion cannula is in the retracted position, wherein the reserve loop is configured to be completely or at least to a large extend diminished when the insertion cannula is in the extended position; or
the reserve loop is formed when the insertion cannula is in the extended position, wherein the reserve loop is configured to be completely or at least to a large extend diminished when the insertion cannula is in the retracted position.

Embodiment 8

The medical device according to any one of the preceding embodiments, wherein the medical device comprises at least one analyte sensor slider, wherein the analyte sensor slider comprises at least one receptacle, wherein the receptacle is configured to receive the reserve loop at least partially when the insertion cannula is in the retracted position.

Embodiment 9

The medical device according to the preceding embodiment, wherein the analyte sensor slider is configured to be movable within the medical device when the insertion cannula is moved from the retracted position in the extended position.

Embodiment 10

The medical device according to any one of the preceding embodiments, wherein the analyte sensor is at least to a large extend made of at least one elastic material.

Embodiment 11

The medical device according to any one of the preceding embodiments, wherein the analyte sensor comprises at least one flexible circuit board.

Embodiment 12

The medical device according to any one of the preceding embodiments, wherein the analyte sensor comprises at least one material selected from the group consisting of: polyimide, particularly polyimide comprising at least one electrically conductive layer; polyethylene terephthalate.

Embodiment 13

The medical device according to any one of the preceding embodiments, wherein the interconnect device comprises a printed circuit board.

Embodiment 14

The medical device according to any one of the preceding embodiments, wherein the electronic component comprises an application-specific integrated circuit.

Embodiment 15

The medical device according to any one of the preceding embodiments, wherein the electronic component comprises at least one of a measurement device configured for performing an electrochemical measurement with the analyte sensor.

Embodiment 16

The medical device according to any one of the preceding embodiments, wherein at least one of the analyte sensor and the insertion cannula at least partially have an essentially rectangular shape.

Embodiment 17

The medical device according to any one of the preceding embodiments, wherein the insertion cannula is selected from the group consisting of: a closed cannula with the wall circumferentially enclosing a lumen of the insertion cannula; a slotted cannula, with the insertion cannula having a slot extending in an axial direction.

Embodiment 18

The medical device according to any one of the preceding embodiments, wherein one part of the analyte sensor, particularly the insertable portion of the analyte sensor, is received in the insertion cannula, wherein one further part of the analyte sensor is located outside of the insertion cannula.

Embodiment 19

The medical device according to the preceding embodiment, wherein the analyte sensor is folded such that the further part of the analyte sensor is located adjacent to the insertion cannula.

Embodiment 20

The medical device according to any one of the preceding embodiments, wherein the insertion cannula is at least partially made of at least one biocompatible material.

Embodiment 21

The medical device according to any one of the preceding embodiments, wherein the insertion cannula is configured such that the insertion cannula is withdrawn into the medical device after insertion of the analyte sensor.

Embodiment 22

The medical device according to any one of the preceding embodiments, wherein the insertion cannula, when being in the extended position, has an angle of 30° to 60°, preferably of 40° to 50°, more preferably of 45°, to a bottom side of the medical device.

Embodiment 23

The medical device according to the preceding embodiment, wherein the bottom side of the medical device comprises at least one adhesive surface configured for attachment of the medical device to a skin site of the user.

Embodiment 24

The medical device according to any one of the preceding embodiments, wherein the medical device comprises at least one housing, wherein the housing comprises at least one electronics unit compartment and at least one insertion cannula compartment, wherein the electronics unit is at least to a large extend received in the electronics unit compartment, wherein the insertion cannula is at least to a large extend received in the insertion cannula compartment when the insertion cannula is in the retracted position.

Embodiment 25

The medical device according to the preceding embodiment, wherein the insertion cannula compartment forms a sealed compartment.

Embodiment 26

The medical device according to any one of the two preceding embodiments, wherein the insertion cannula compartment is configured to provide a sterile compartment at least for the insertable portion of the analyte sensor.

Embodiment 27

The medical device according to any one of the three preceding embodiments, wherein the insertion cannula compartment comprises at least one opening, particularly at least one passage opening, wherein the insertion cannula is movable from the insertion cannula compartment into the body tissue through the passage or vice versa.

Embodiment 28

The medical device according to the preceding embodiment, wherein the opening is covered via at least one sealing element providing a sterile packaging of the insertion cannula compartment.

Embodiment 29

The medical device according to any one of the two preceding embodiments, wherein a shape of the opening corresponds to a shape of the insertion cannula.

Embodiment 30

The medical device according to any one of the six preceding embodiments, wherein the insertion cannula compartment comprises at least one detachable cap.

Embodiment 31

The medical device according to the preceding embodiment, wherein the insertion cannula is received in the detachable cap after insertion of the analyte sensor, wherein the detachable cap is configured to be detachable from the medical device after insertion of the analyte sensor.

Embodiment 32

The medical device according to any one of the eight preceding embodiments, wherein the insertion cannula compartment and the electronics unit compartment are separated by at least one separating wall.

Embodiment 33 The medical device according to the preceding embodiment, wherein the separating wall comprises at least one analyte sensor receptacle, wherein an intermediate portion of the analyte sensor is received in the analyte sensor receptacle.

Embodiment 34

The medical device according to the preceding embodiment, wherein the intermediate portion of the analyte sensor is received in the analyte sensor receptacle such that at least the connector portion of the analyte sensor is located in the electronics unit compartment and such that at least the insertable portion of the analyte sensor is received in the insertion cannula compartment.

Embodiment 35

The medical device according to any one of the two preceding claims, wherein the analyte sensor receptacle is tightly sealed from a surrounding environment by at least one of an adhesive; a sealing element, particularly a sealing element made of at least one thermoplastic elastomer; a heat-sealing; a screw connection; grouting.

Embodiment 36

The medical device according to any one of the twelve preceding embodiments, wherein the analyte sensor is partially received in the insertion cannula compartment, wherein the analyte sensor is partially received in the electronics unit compartment.

Embodiment 37

The medical device according to any one of the preceding embodiments, wherein the analyte sensor is an electrochemical sensor.

Embodiment 38

The medical device according to the preceding embodiment, wherein the active portion of the analyte sensor comprises at least two sensor electrodes.

Embodiment 39

The medical device according to any one of the two preceding embodiments, wherein the connector portion of the analyte sensor comprises at least two electrical contacts.

Embodiment 40

The medical device according to any one of the preceding embodiments, wherein the active portion of the analyte sensor is part of the insertable portion of the analyte sensor or vice versa.

Embodiment 41

The medical device according to any one of the preceding embodiments, wherein the analyte sensor is a transcutaneous sensor.

Embodiment 42

Method of using a medical device according to any one of the preceding embodiments, wherein the method comprises:
i. placing the medical device onto a skin site of the user, with the insertion cannula being in the retracted position;
ii. extending the insertion cannula into the extended position, whereby a shape of the reserve loop is altered as the active portion advances into the body tissue; and
iii. retracting the insertion cannula into the retracted position, with the active portion remaining in the body tissue.

Embodiment 43

The method according to the preceding embodiment, wherein the medical device is at least partially provided as a sterile packaging before usage.

Embodiment 44

The method according to any one of the two preceding embodiments, wherein the step of extending the insertion cannula into the extended position is conducted via at least one insertion aid.

Embodiments 45: The method according to any one of the three preceding embodiments, wherein the insertion cannula comprises at least one insertion cannula slider, wherein the insertion cannula is extended into the extended position via moving the insertion cannula slider within the insertion cannula compartment towards the skin site.

Embodiment 46

The method according to any one of the four preceding embodiments, wherein the altering of the shape of the reserve loop comprises a diminishing of the reserve loop.

Embodiments 47

The method according to any one of the five preceding embodiments, wherein the altering of the shape of the reserve loop comprises a magnifying or a forming of the reserve loop.

Embodiments 48

Method for assembling a medical device according to any one of the preceding embodiments relating to a medical device, wherein the method comprises:
a. providing a housing of the medical device, the housing comprising at least one insertion cannula compartment and at least one electronics unit compartment;
b. placing the analyte sensor into the housing, wherein the active portion and the reserve loop are at least partially placed in the insertion cannula compartment and the connector portion is at least partially placed in the electronics unit compartment;
c. sterilizing the insertion cannula compartment; and
d. electrically connecting the electronics unit to the passive portion of the analyte sensor.

Embodiment 49

The method according to the preceding embodiment, wherein the step of sterilizing the insertion cannula compartment comprises a radiation sterilization, particularly e-beam sterilization.

Embodiment 50

The method according to any one of the two preceding embodiments, the method further comprising at least one step of sterilizing the electronics unit compartment.

Embodiment 51

The method according to the preceding embodiment, wherein the step of sterilizing the electronics unit comprises a gas sterilization.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

DETAILED DESCRIPTION OF THE EMBODIMENTS

Figure 1:
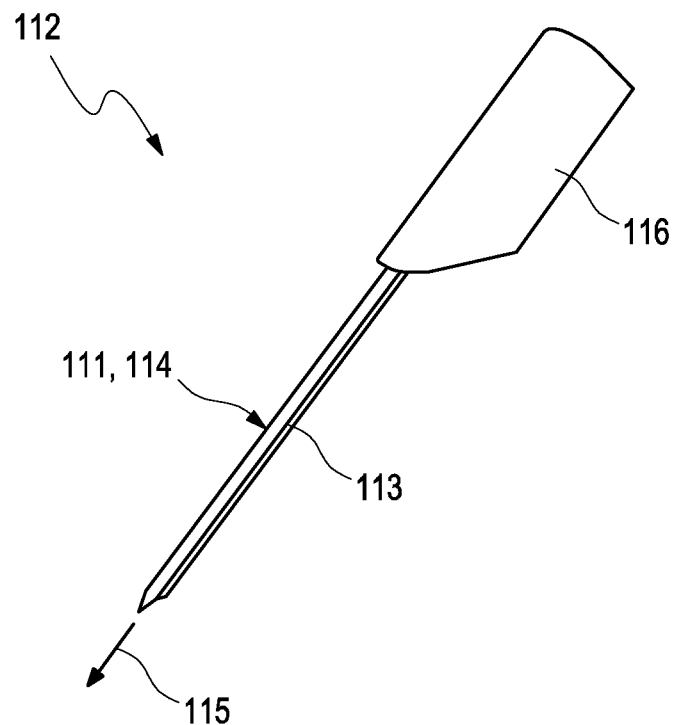
FIGS. 1A to 1M show an exemplary embodiment of a method for assembling a medical device.
Figure 1:
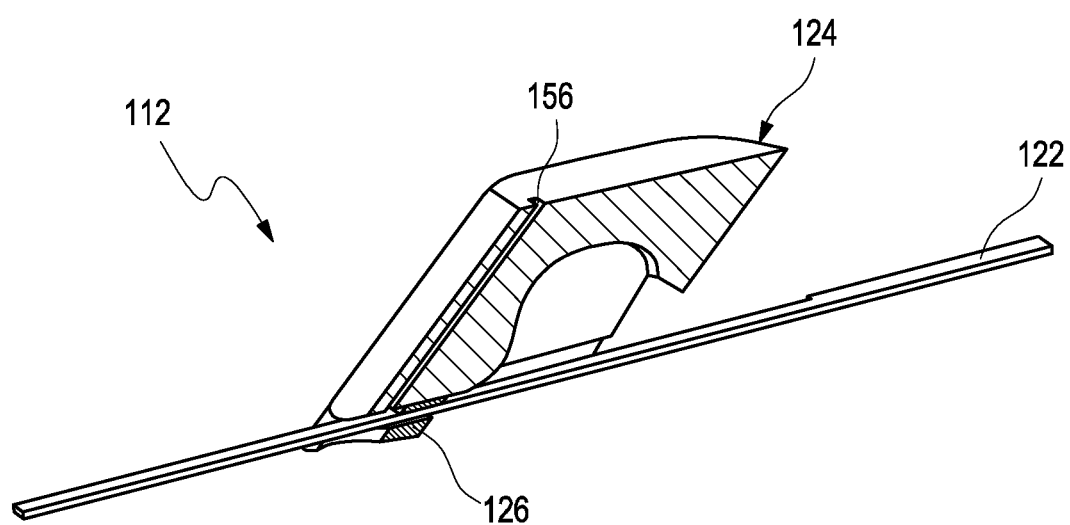
Figure 1:
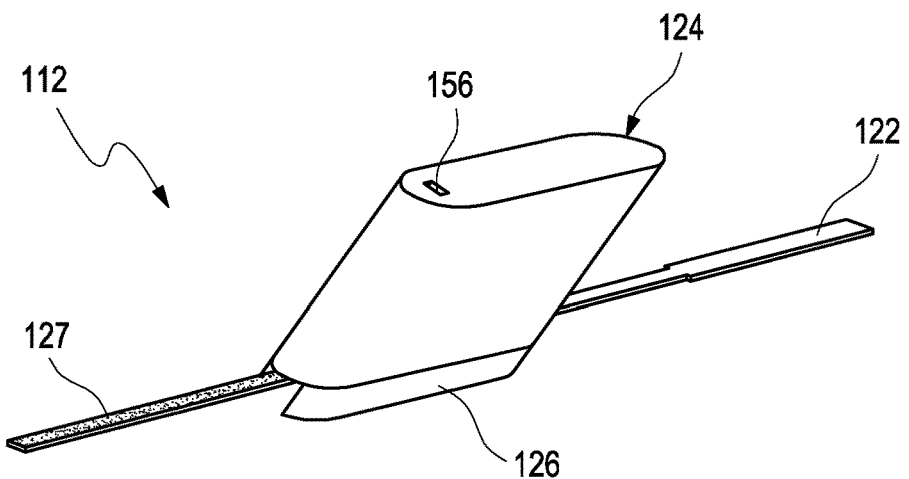
Figure 1:
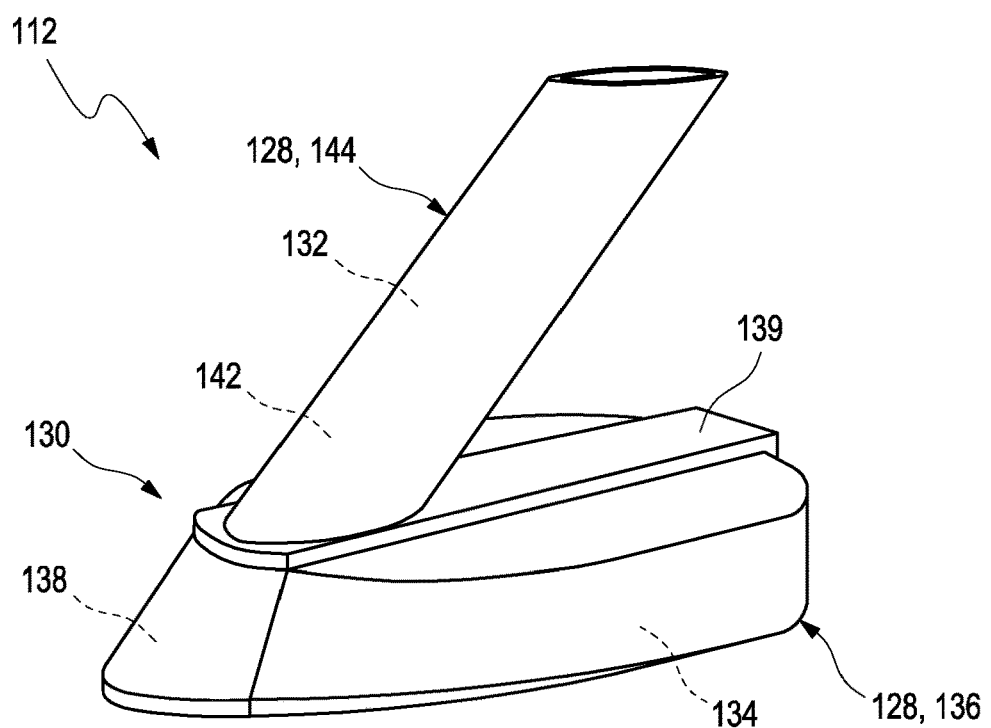
Figure 1:
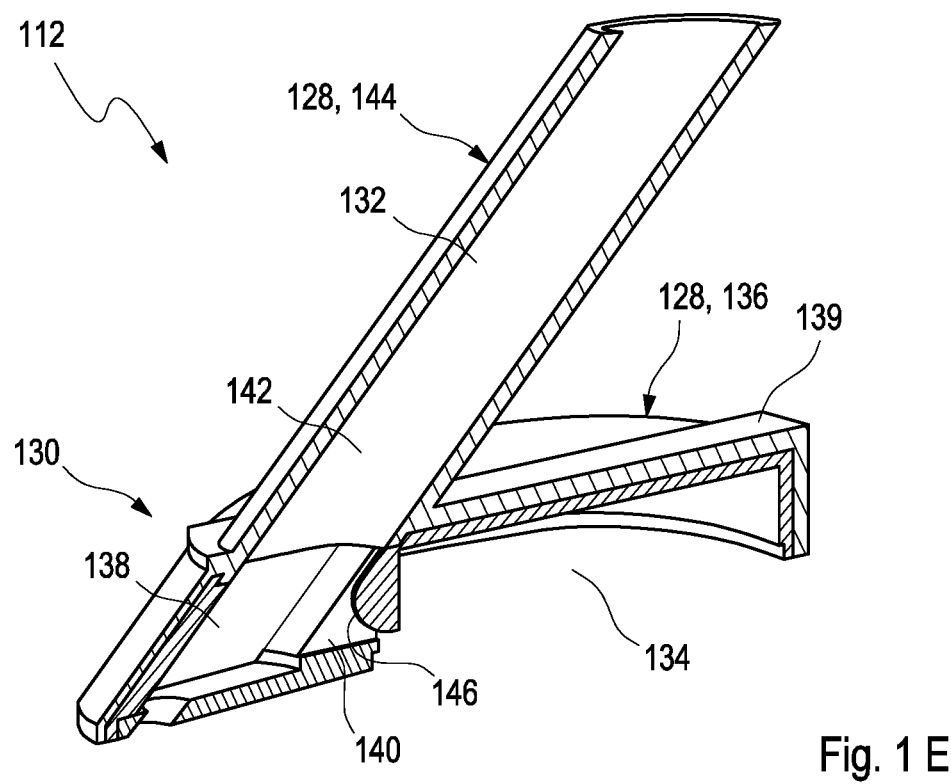
Figure 1:
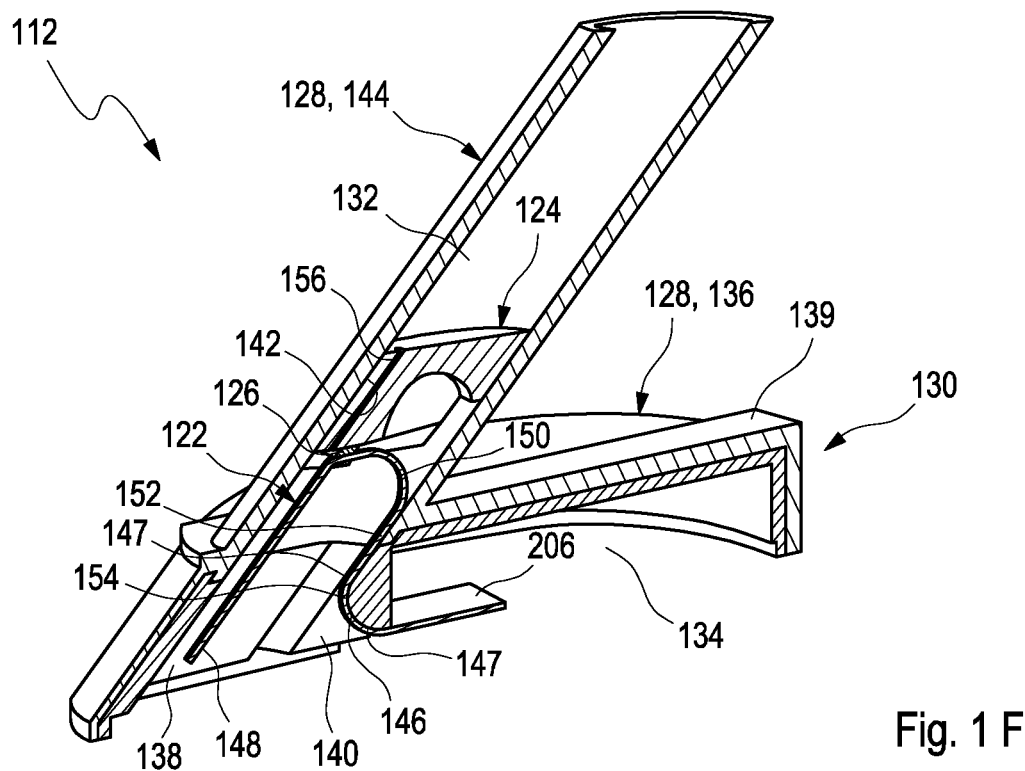
Figure 1:
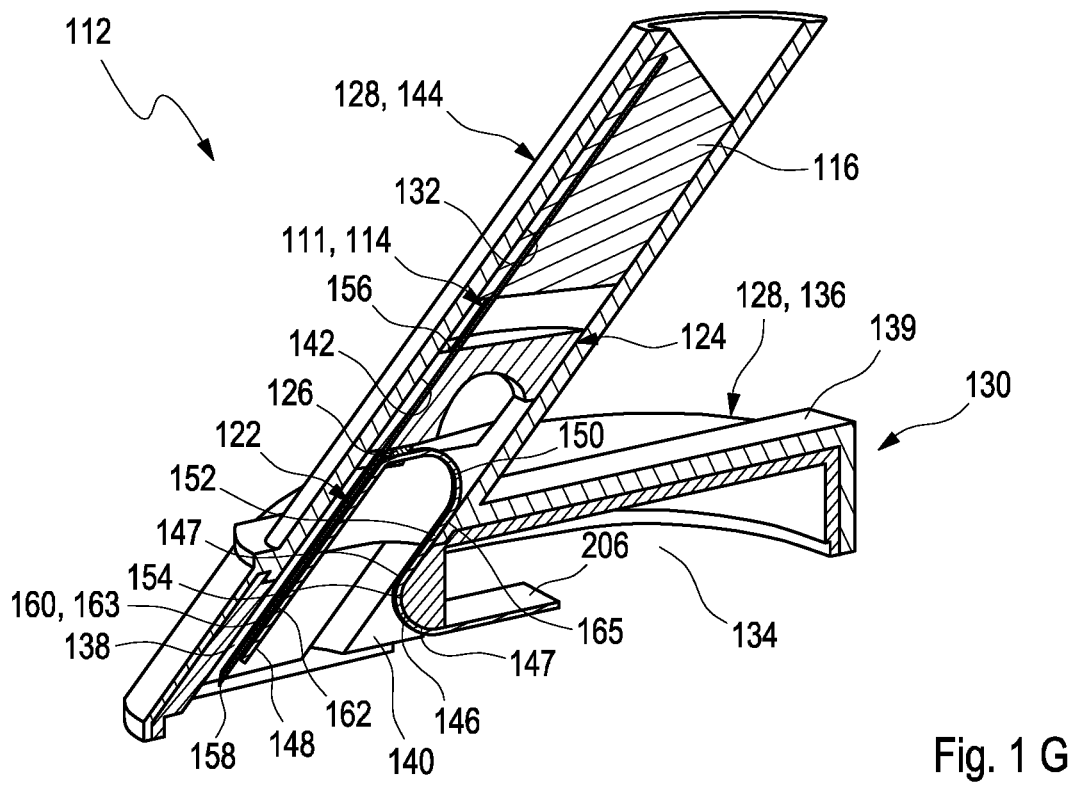
Figure 1:
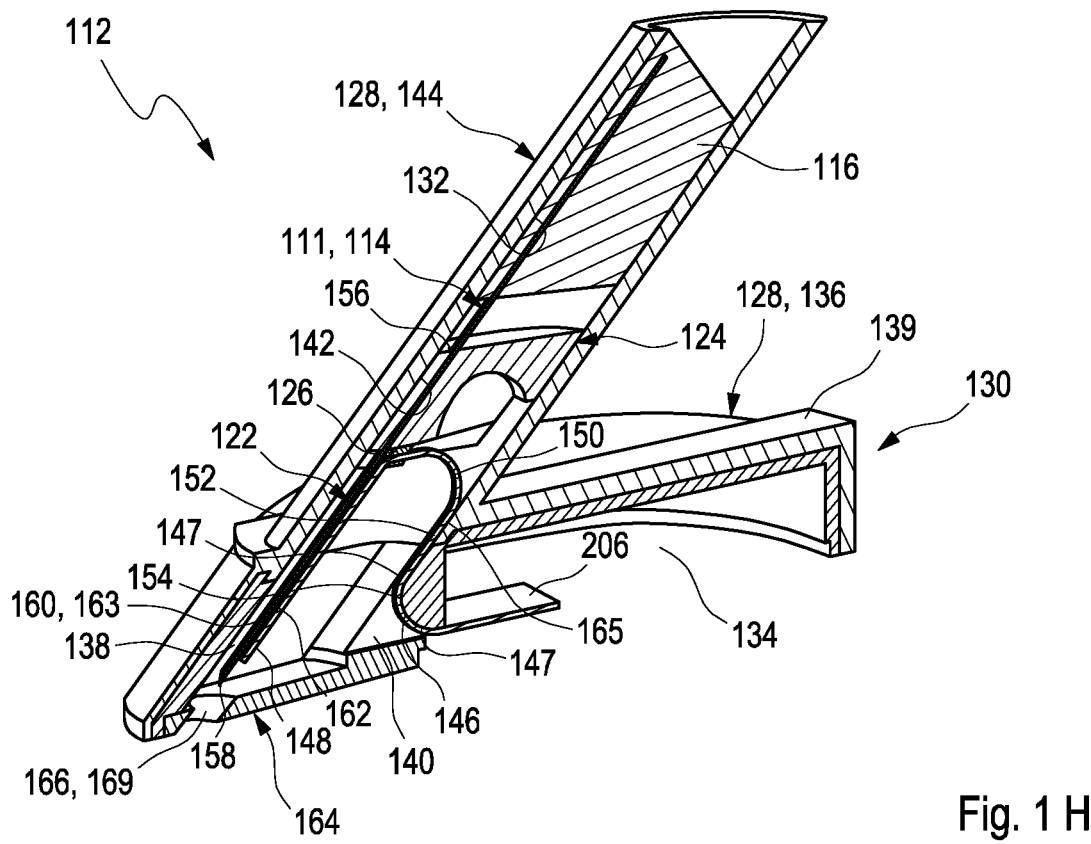
Figure 1:
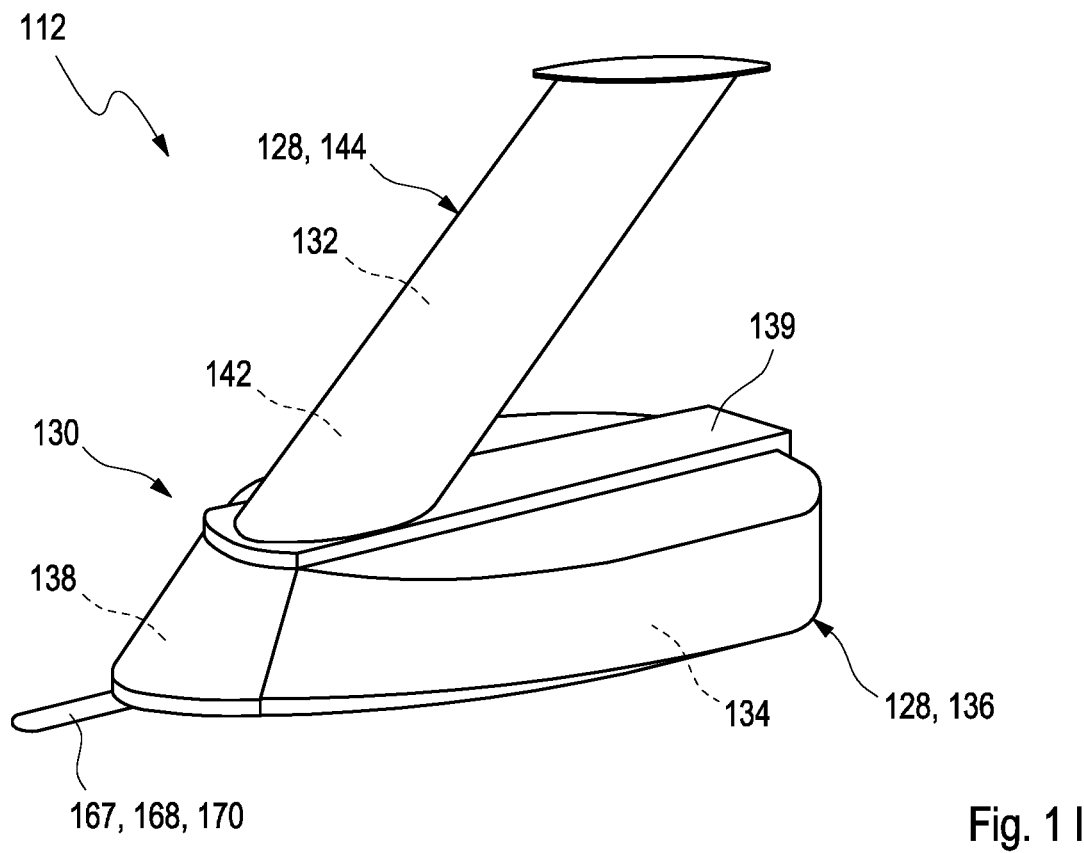
Figure 1:
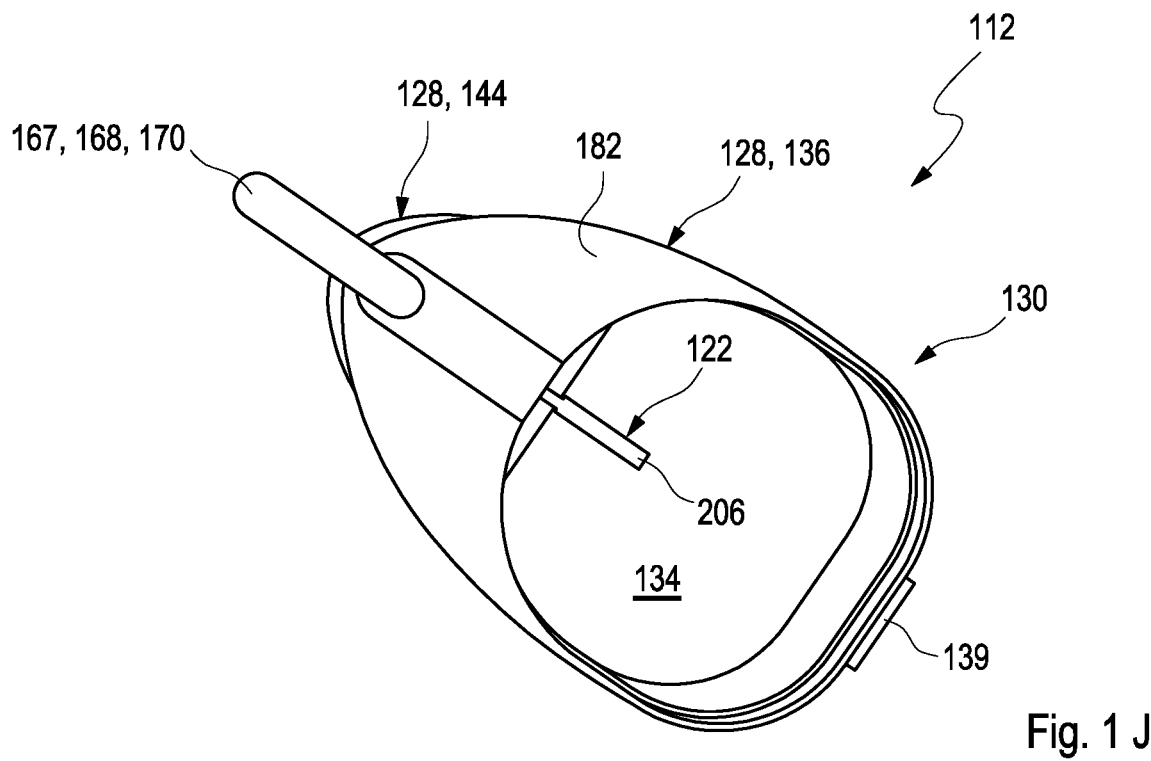
Figure 1:
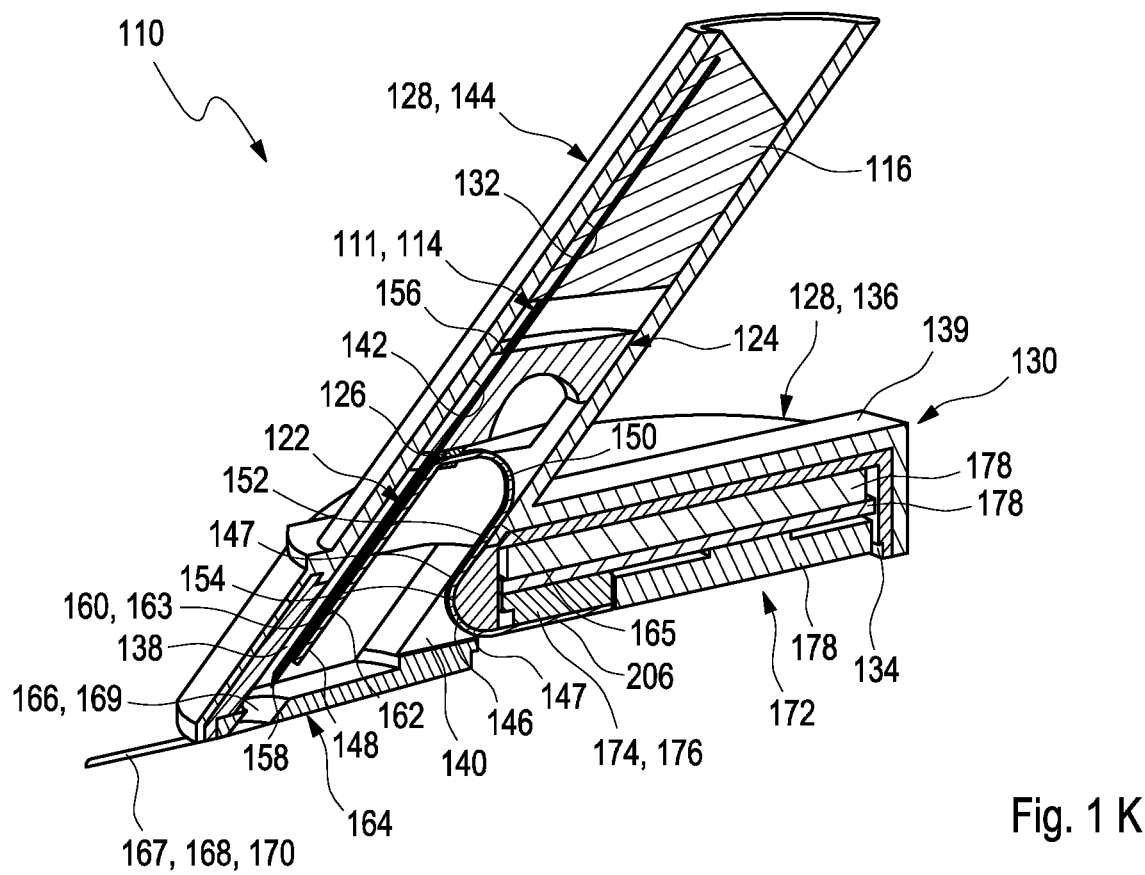
Figure 1:
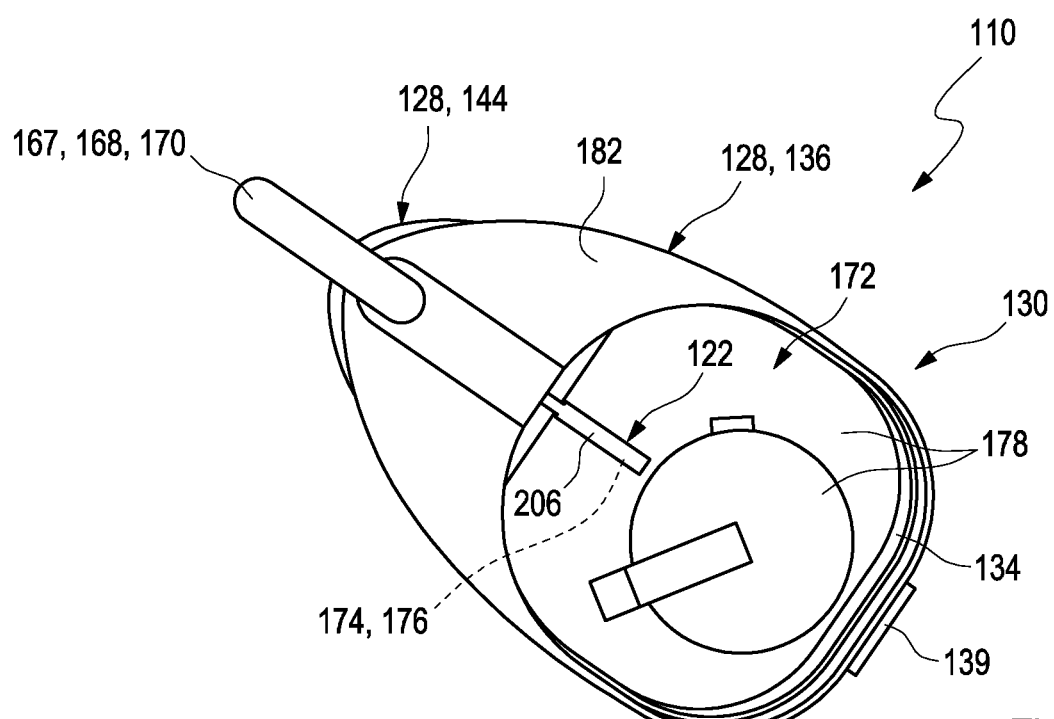
Figure 1:
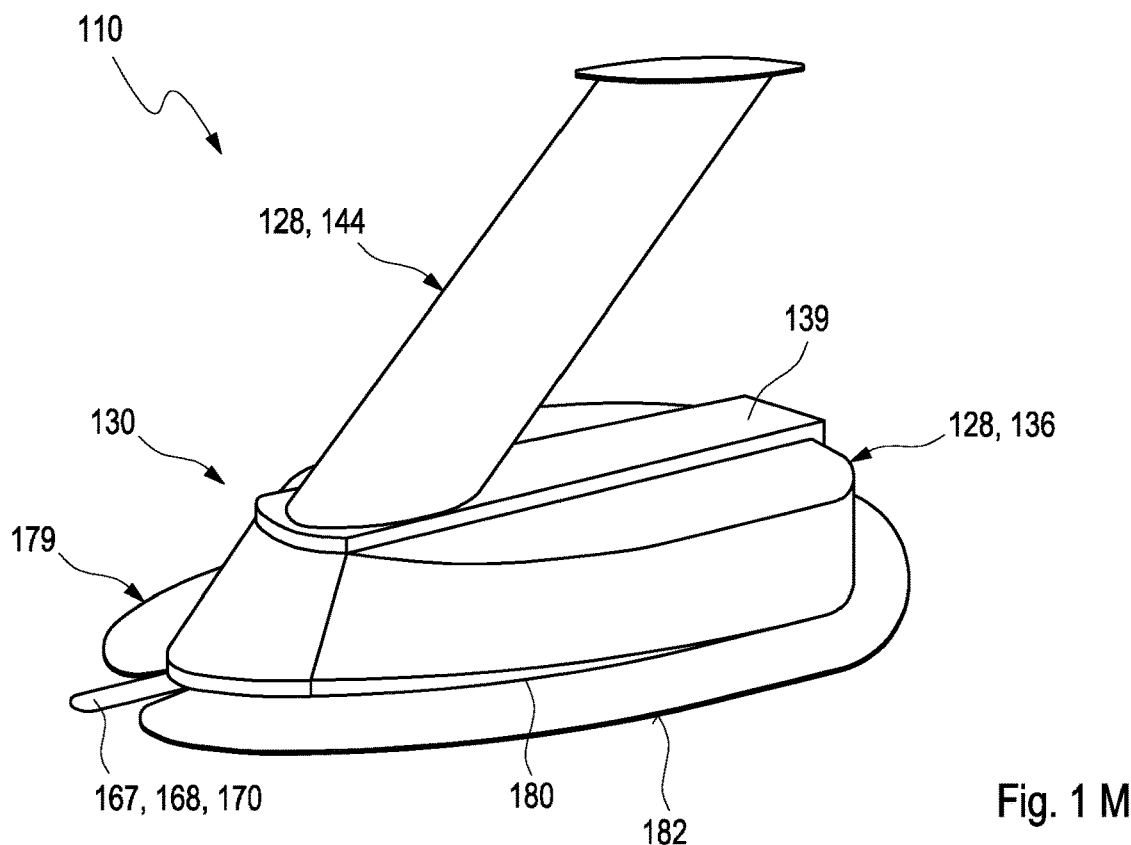
Figure 2:
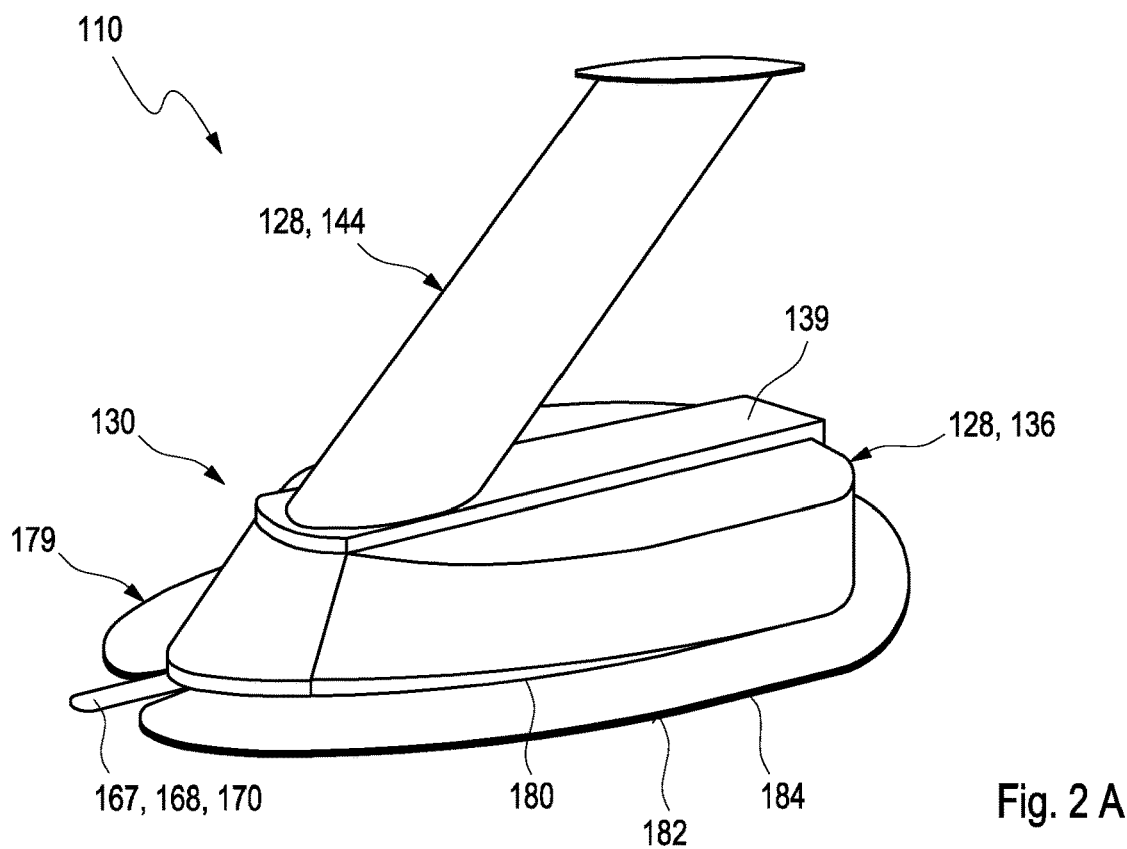
FIGS. 2A to 2D show an exemplary embodiment of a method of using a medical device.
Figure 2:
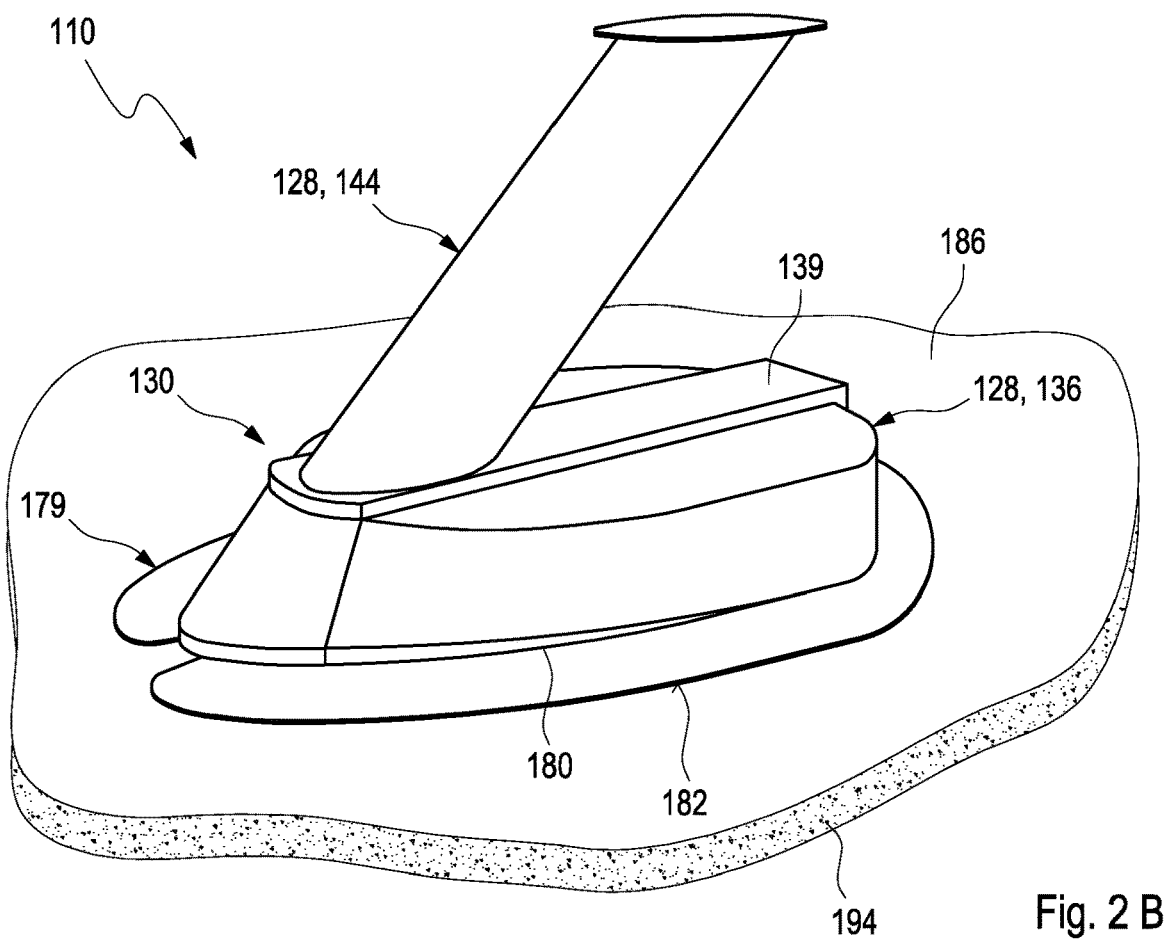
Figure 2:
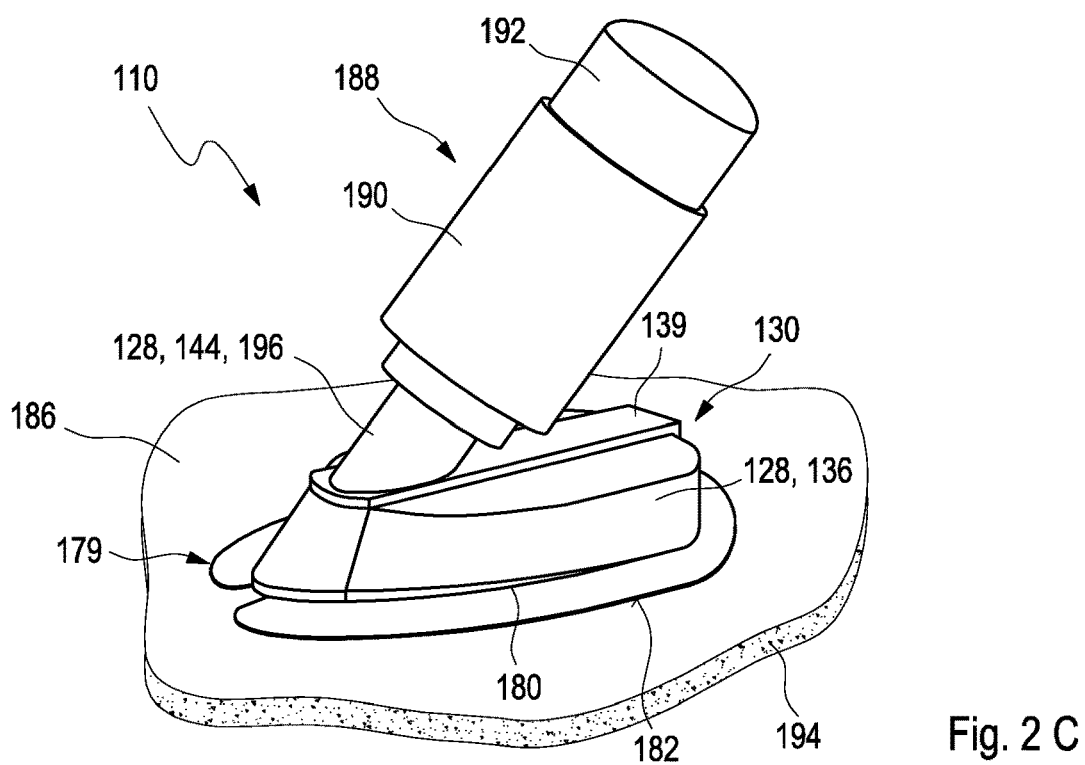
Figure 2:
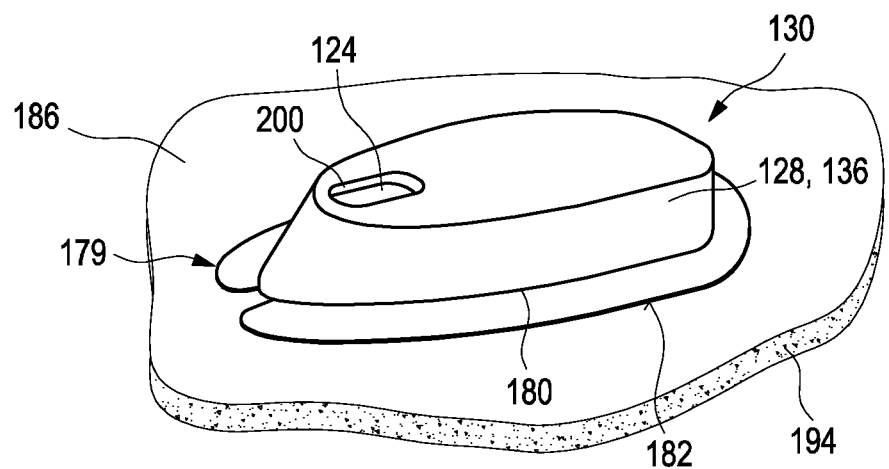

FIGS. 1A to 1M show an exemplary embodiment of a method for sampling a medical device 110. The medical device 110 is depicted in FIGS. 1K to 1M. In FIG. 1K, the medical device 110 is illustrated in a cross-section of view. In FIGS. 1L to 1M, the medical device 110 is illustrated in different perspective views, respectively. In FIGS. 1A to 1J, various intermediate products 112 of the medical device 110 are shown.

Firstly, as depicted in FIG. 1A, an insertion cannula 114 may be provided. The insertion cannula 114 may be fixedly attached to a insertion cannula slider 116. Specifically, the insertion cannula 114 may be a slotted cannula 111 with the insertion cannula 114 having a slot 113 extending in an axial direction 115.

In a further step, as illustrated in FIGS. 1B and 1C, an analyte sensor 122 may be provided. The analyte sensor 122 may be fixedly attached to an analyte sensor slider 124. Specifically, as depicted in FIG. 1B, the analyte sensor 122 may be received in a receptacle 126 of the analyte sensor slider 124. Further, as illustrated in FIG. 1C, the analyte sensor 122 may at least partially be equipped with a biocompatible coating 127. This may exemplarily be conducted via at least one dip coating process. However, other procedures may also be feasible.

In a further step, as illustrated in FIGS. 1D and 1E, parts 128 of a housing 130 of the medical device 110 may be provided. The housing 130 comprises at least one insertion cannula compartment 132 and at least one electronics unit compartment 134. Exemplarily, the housing 130 may be manufactured by injection molding. The electronics unit compartment 134 may be manufactured as one first component 136. Further, the first component 136 may provide a section 138 of the insertion cannula compartment 132. The section 138 may be separated from the electronics unit compartment 134 by a separating wall 140. A further section 142 of the insertion cannula compartment 132 may be provided as a second component 144. The second component 144 may be fixedly attached to the first component 136. Exemplarily, the second component 144 may be positively attached to the first component 136 via a clamp 139.

In a further step, as illustrated in FIG. 1F, the analyte sensor 122 is placed into the housing 120 of the medical device 110. The separating wall 140 may have a separating wall receptacle 146. The analyte sensor 122 may be placed into the housing 120 such that an active portion 148, a passive portion 152 and a reserve loop 150 of the analyte sensor 122 are at least partially placed in the insertion cannula compartment 132 whereas the connector portion 206 of the analyte sensor 122 may be at least partially placed in the electronics unit compartment 134. Thereby an intermediate portion 154 of the analyte sensor 122 may be placed within the separating wall receptacle 146. The separating wall receptacle 146 may be sealed via at least one adhesive 147.

In a further step, as depicted in FIG. 1G, insertion cannula 114 may be placed into the housing 120. Specifically, the insertion cannula 114 may be placed in the insertion cannula compartment 132. The insertion cannula 114 may be received in an insertion cannula receptacle 156 of the analyte sensor slider 124. The insertion cannula receptacle 156 may fully penetrate the analyte sensor slider 124 such that an end 158 of the insertion cannula 114 may be received within the section 138 wherein the insertion cannula slider 116 may be located in the further section 142. Further, the insertion cannula 114 may be received in the insertion cannula compartment 132 such that an insertable portion 160 of the analyte sensor 122 is received in a lumen 162 of the insertion cannula 114. Consequently, one part 163 of the analyte sensor 122, particularly the insertable portion 160, may be received in the insertion cannula 114 and one further part 165 of the analyte sensor 122 may be located outside of the insertion cannula 114.

In a further step, as illustrated in FIG. 1H, the insertion cannula compartment 132 may be sealed by a cover element 164. The cover element 164 may be fixedly attached to the first component 136. Cover element 164 may comprise an opening 166, specifically a passage opening 169. The cover element 166 may be configured such that the insertion cannula 114 is enabled to penetrate the insertion cannula compartment 132 via the opening 166.

In a further step, as depicted in FIGS. 1I and 1J, the cover element opening 166 may be sealed with at least one sealing element 167. Exemplarily, the sealing element 167 may be a sealing foil 168 such as a sealing film 170. Thereafter, the insertion cannula compartment 132 is sterilized. A sterilization process may be based on radiation, particularly on e-beam sterilization. The method may further comprise at least one step of sterilizing the electronics unit 172, particularly by gas sterilization such as by using ethylene oxide.

In a further step, as illustrated in FIGS. 1K and 1L, an electronics unit 172 may be placed into the electronics unit compartment 134. The electronics unit 172 is electrically connected to the passive portion 152 of the analyte sensor 122. The electronics unit 172 comprises at least one interconnect device 174 such as a printed circuit board 176 for operably connecting to the analyte sensor 122. Further, the electronics unit 172 comprises at least one electronic component 178 attached to the interconnect device 174.

In further step, as illustrated in FIG. 1M, the electronics unit compartment 134 may be sealed with an electronics unit cover element (not shown), and at least one adhesive element 179 may be fixedly attached to a bottom side 180 of the housing 120. The adhesive element 179 may specifically have at least one adhesive surface 182 and may thus be configured for attaching the medical device 110 to a skin site of a user or a patient.

FIGS. 2A to 2D show an exemplary embodiment of a method of using a medical device 110. The medical device 110, as illustrated in FIGS. 2A to 2D, is illustrated in different perspective views, respectively. The medical device 110 corresponds at least in large parts to the medical device 110 as illustrated in FIGS. 1K to 1M. Thus, reference may be made to the description of FIGS. 1K to 1M above.

Firstly, the medical device 110, as illustrated in FIG. 2A, may be removed from a packaging (not shown) by the user or the patient. Secondly, as illustrated in FIG. 2B, the sealing element 167 may be removed from the cover element 164. Further, the adhesive surface 182 of the adhesive element 179 may be exposed. Thereby, an adhesive surface cover element 184 may be removed from the adhesive surface 182. The medical device 110 may be placed onto a skin site 186 of the user when the insertion cannula 114 is in a retracted position.

Further, as illustrated in FIG. 2C, the insertion cannula 114 is extended in an extended position. This may be conducted via an insertion aid 188. The insertion aid 188 may be configured to support the extending of the insertion cannula 114. The insertion aid 188 may have an insertion aid receptacle 190. The insertion aid receptacle 190 may have a shape with corresponds to the insertion cannula compartment 132. Further, the insertion aid 188 may have a button 192 which may be pressable by the user or the patient. The button 192 may be configured to trigger an insertion mechanism thereby extending the insertion cannula 114 into the extended position. Thereafter, the insertion cannula 114 may be retracted into the retracted position with the active portion 148 of the analyte sensor 122 in the body tissue 194. The insertion aid 188 as well as a detachable cap 196 of the insertion cannula compartment 132 may be detached from the housing 120.

The medical device 110, as depicted in FIG. 2D, an opening 200 of the housing 130 of the medical device 110 which is formed after removing the detachable cap 196 may be sealed via the analyte sensor slider 124. Optionally, the medical device 110 may afterwards be covered by a protective element (not shown).

Figure 3:
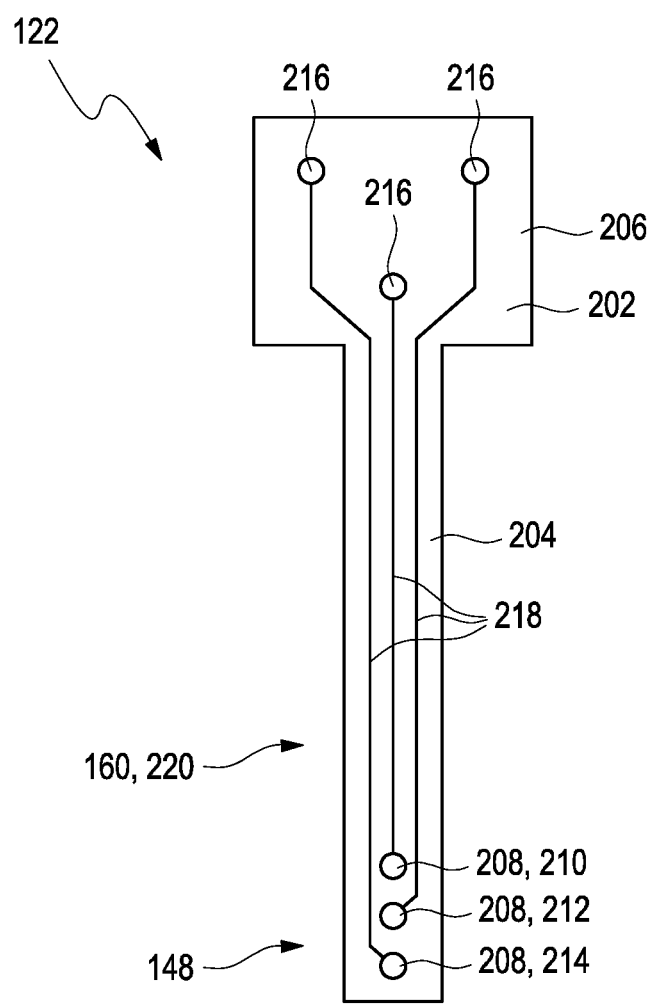
FIGS. 3A to 3C show an exemplary embodiment of an analyte sensor in a top view (FIG. 3A) and an exemplary embodiment of a medical device in different cross-sectional views (FIGS. 3B and 3C)
Figure 3:
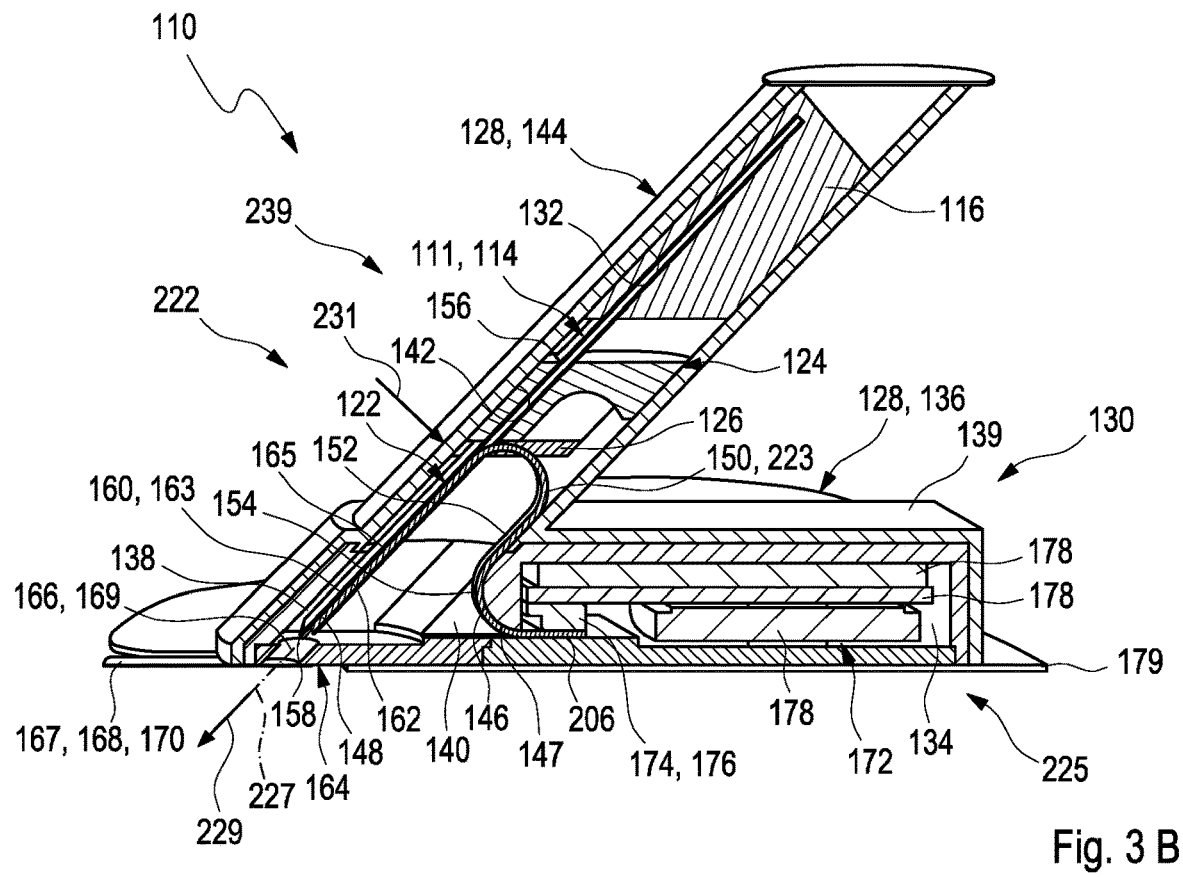
Figure 3:
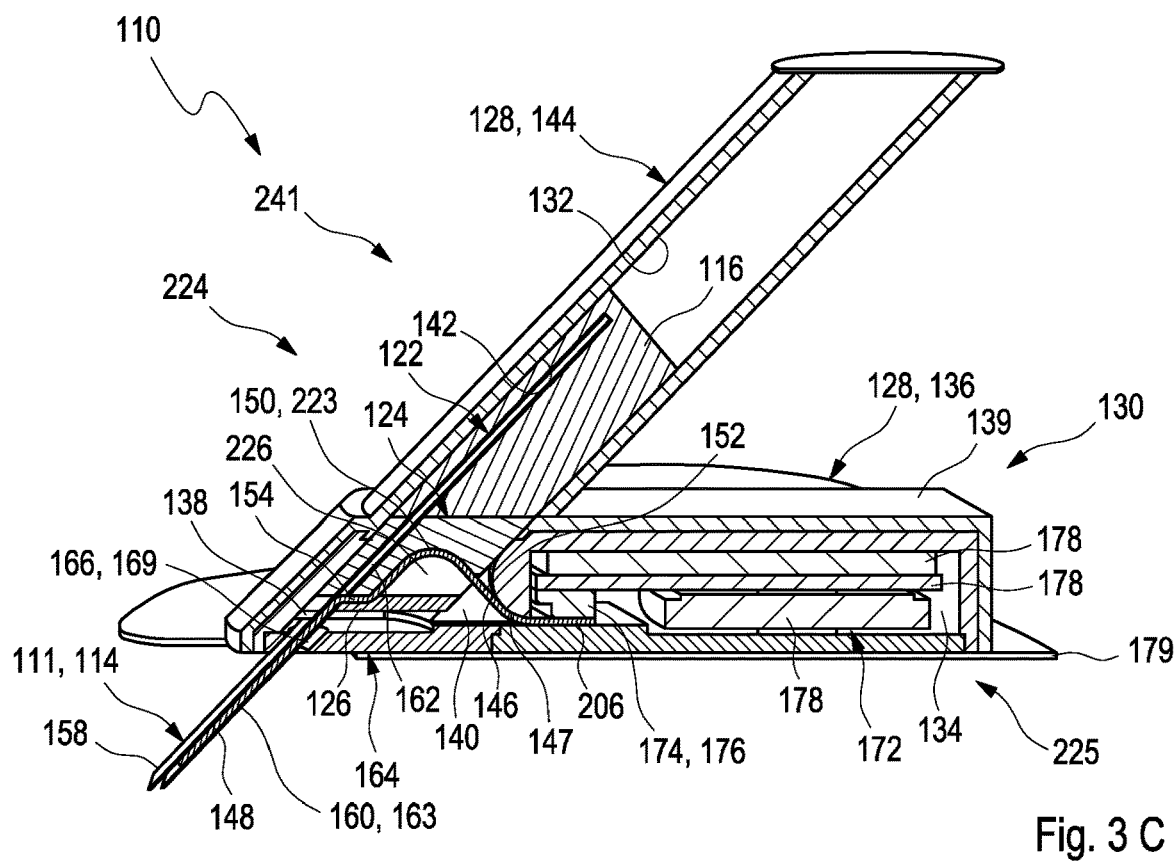

FIGS. 3A to 3C show an exemplary embodiment of an analyte sensor 122 in a top view (FIG. 3A), and an exemplary embodiment of a medical device 110 in different cross-sectional views (FIGS. 3B to 3C). The medical device 110 corresponds at least in large parts to the medical device 110 as illustrated within FIGS. 1A to 2D. Thus, reference may be made to the description of FIGS. 1A to 2D above.

The analyte sensor 122 as illustrated in FIG. 3A may comprise at least one substrate 202. The substrate 202 may comprise a shaft 204 having an elongate shape and the connector portion 206. Further, the analyte sensor 122 may comprise three sensor electrodes 208. Exemplarily, the sensor electrodes 208 may comprise one working electrode 210, one reference electrode 212 and one counter electrode 214. Further, the connector portion 206 may comprise electrical contacts 216. The electrical contacts 216 may be connected to the sensor electrodes 208 via electrical traces 218. The sensor electrodes 208 may form the active portion 148. The active portion 148 may be configured for detecting at least one analyte in a body fluid. The electrical contacts 216 may form the passive portion 152 of the analyte sensor 122. The passive portion 152 may be configured for being electrically connectable to the electronics unit 172. At least one part 220 of the shaft 204 may form the insertable portion 160 of the analyte sensor. The insertable portion 160 may be configured for being transcutaneously inserted into the body tissue 194 of the user of the patient. The active portion 148 may be part of the insertable portion 160.

FIGS. 3B and 3C show the medical device 110 in different cross-sectional views, respectively. The insertion cannula 114 is movable in between at least one retracted position 222, as illustrated in FIG. 3B, and at least one extended position 224, as illustrated in FIG. 3C. Thereby, the electronics unit 172 remains in a fixed position 225 when the insertion cannula 114 is moved from the extended position 224 to the retracted position 222 or vice versa. When the insertion cannula 114 is in the retracted position 222, as illustrated in FIG. 3B, the passive portion 152 forms in between the connector portion 206 and the active portion 148, the at least one reserve loop 150 configured for compensating for an insertion path during movement from the retracted position 222 into the extended position 224. The reserve loop 150 may be at least to a large extent received within the insertion cannula compartment 132. Specifically, the reserve loop 150 may have a basic shape which corresponds to an oval shape. Thus, the reserve loop 150 may have an appearance which corresponds to an oval or at least to parts of an oval. The reserve loop 150 may comprise at least one folded section 223 of the analyte sensor 122. Specifically, the insertion cannula 114 may comprise at least one major axis 227 which extends along a direction of extension 229 of the insertion cannula 114 and the folded section 223 of the analyte sensor 122 may be folded in a direction 231 transverse to the major axis 227.

When the insertion cannula 114 is in the extended position, as illustrated in FIG. 3C, the insertable portion 160 of the analyte sensor 122 may be extended through the opening 166 and may be received in the body tissue (not shown) of the user or the patient. The reserve loop 150 may be diminished. Thus, a portion of the analyte sensor 122, which contributes to the reserve loop 150 may be decreased. Thereafter, the reserve loop 150 may be received in a reserve loop receptacle 226 of the analyte sensor slider 124.

Figure 4:
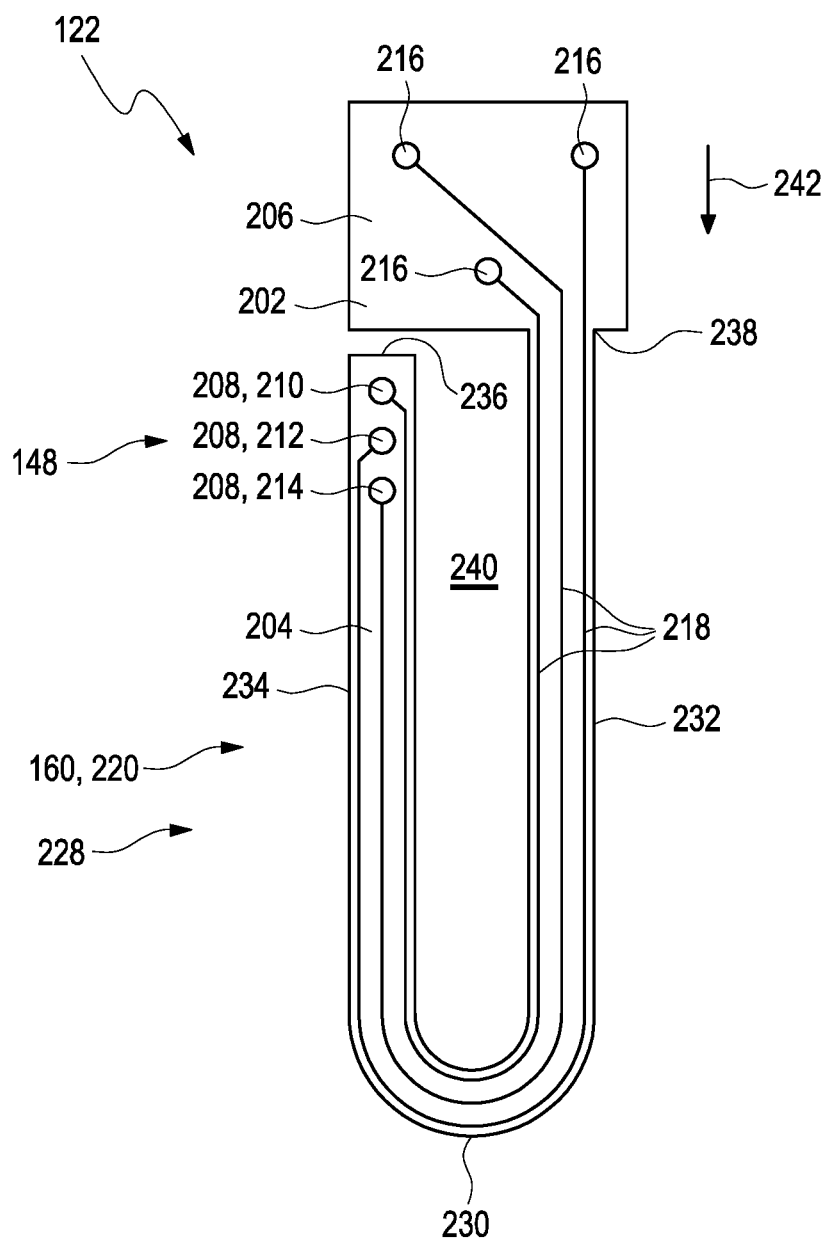
FIGS. 4A to 4C show an exemplary embodiment of an analyte sensor in a top view (FIG. 4A) and an exemplary embodiment of a medical device in different cross-sectional views (FIGS. 4B and 4C)
Figure 4:
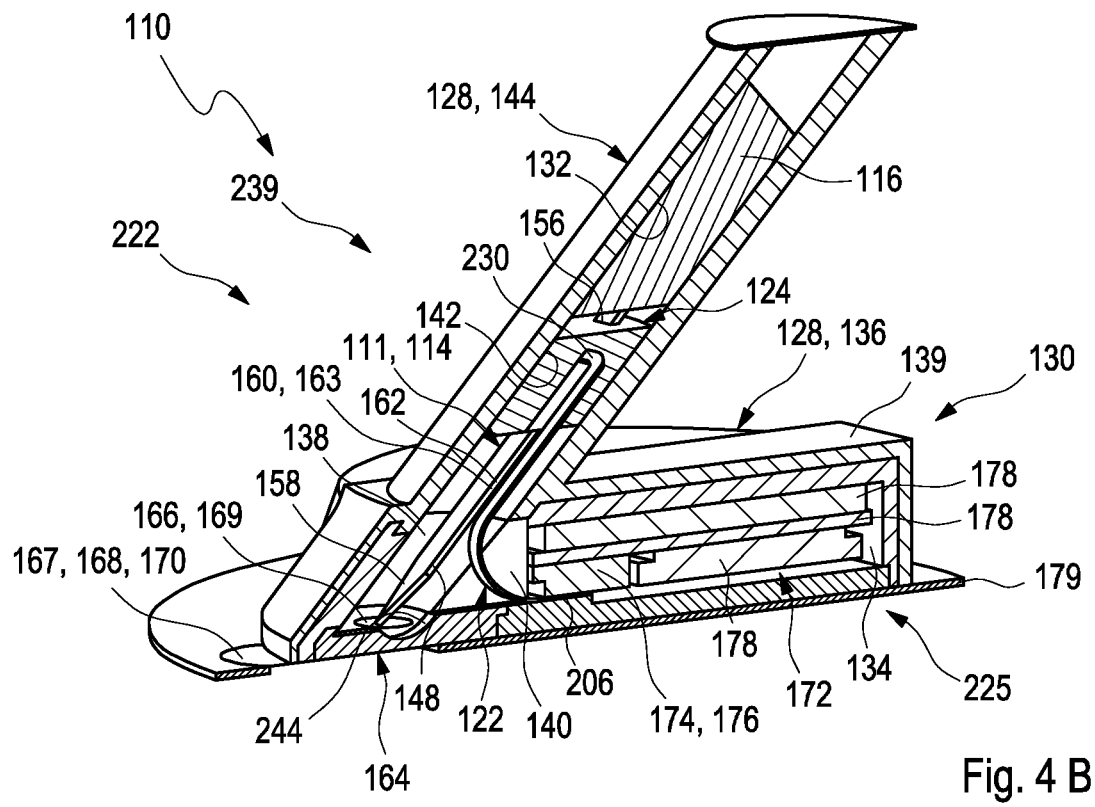
Figure 4:
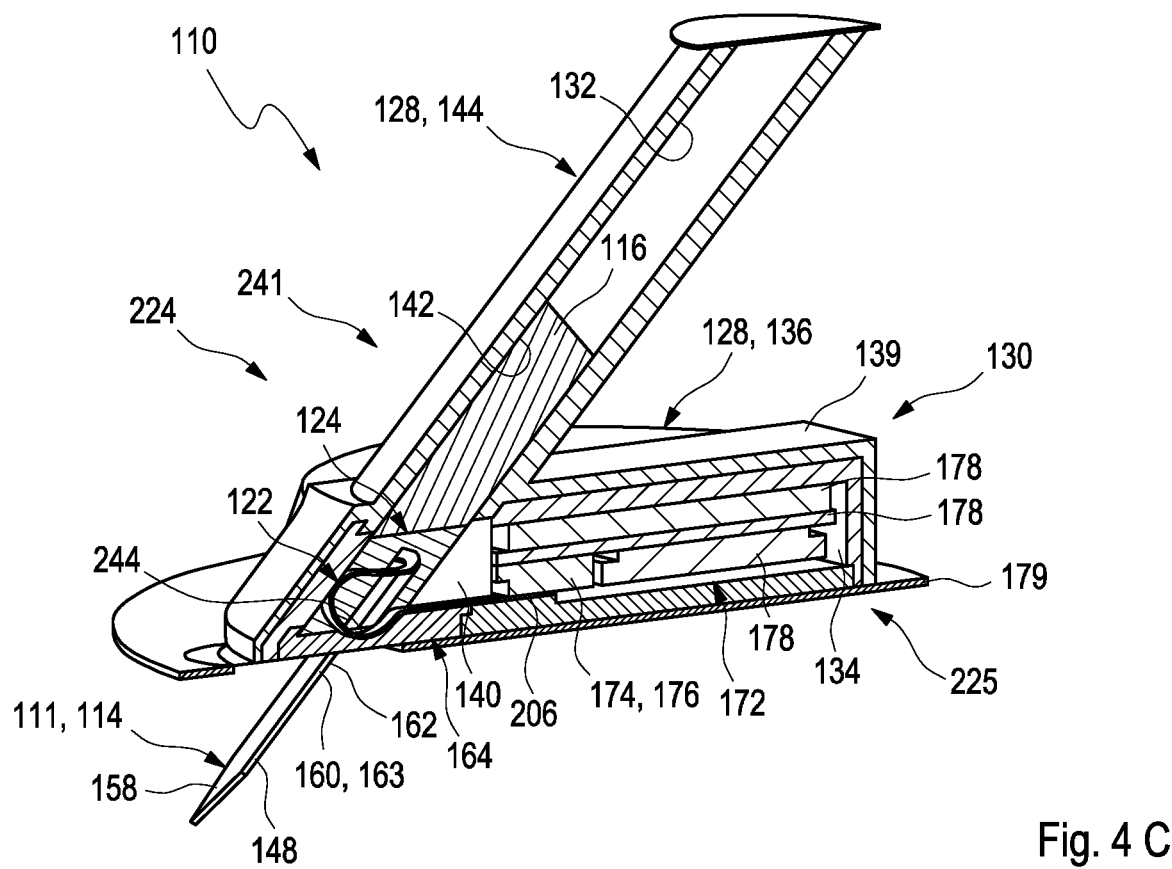

FIGS. 4A to 4C show an exemplary embodiment of an analyte sensor 122 depicted in a top view (FIG. 4A), and a medical device 110 illustrated in different cross-sectional views (FIGS. 4B and 4C). The analyte sensor 122 and the medical device 110 correspond partially to the analyte sensor 122 and to the medical device 110 as depicted in FIGS. 3A to 3C. Thus, reference may be made to the description of FIGS. 3A to 3C above.

The analyte sensor 122 may comprise the shaft 204. The shaft 204 may have an elongate shape. Additionally, the shaft 204 may be present in a fold-back structure 228. Thus, the shaft 204 may have a shaft loop 230. The shaft loop 230 may be formed in between a first part 232 of the shaft 204 and a second part 234 of the shaft 204. The first part 232 of the shaft 204 and the second part 234 of the shaft 204 may at least almost have a same length. Thus, a first end 236 of the shaft 204 may be located opposite a second end 238 of the shaft 204 adjacent to the connector portion 206 of the analyte sensor 122. Consequently, the shaft 204 may be existent in a layer 240 defined by a direction of extension 242 of the connector portion 206. The shaft loop 230 may be formed within the layer 240 and also the second part 234 may be present within the layer 240.

FIGS. 4B and 4C show the medical device 110 in different cross-sectional views, respectively. The insertion cannula 114 is movable in between at least one retracted position 222, as illustrated in FIG. 4B, and at least one extended position 224, as illustrated in FIG. 4C. When the insertion cannula 114 is in the retracted position 222, the analyte sensor 122 may be stored in a first shape configuration 239 and when the insertion cannula 114 is in the extended position 224, the analyte sensor 122 may be in a second shape configuration 241. When the insertion cannula 114 is in the retracted position 222, as illustrated in FIG. 4B, no reserve loop may be 150 be present. The insertion cannula 114 may have the shaft loop 230 and a curved section 244 due to guidance of the analyte sensor 122 through the analyte slider receptacle 146.

When the insertion cannula 114 is in the extended position, as illustrated in FIG. 4C, the insertable portion 160 of the analyte sensor 122 may be extended through the opening 166 and may be received in the body tissue (not shown) of the user or the patient. The reserve loop 150 may be formed. Thus, the reserve loop 150 may be generated when the insertable portion 160 of the analyte sensor 122 may be extended through the opening 166. The reserve loop 150 may be at least to a large extent received within the insertion cannula compartment 132. Further, the reserve loop 150 may be received in a cover element receptacle 246 of cover element 184. Specifically, the reserve loop 150 may have a basic shape which corresponds to a circular shape. Thus, the reserve loop 150 may have an appearance which corresponds to a circle or at least to parts of a circle.

Figure 5:
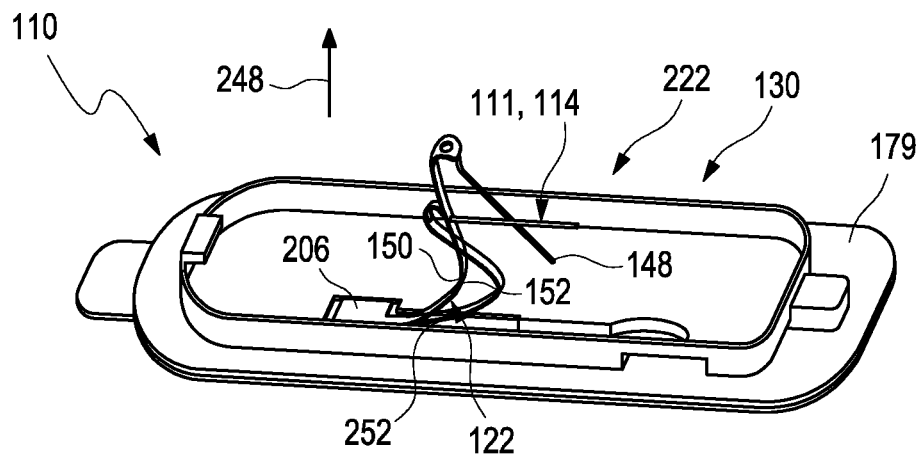
FIGS. 5A to 5B show an exemplary further embodiment of a medical device in a perspective view.
Figure 5:
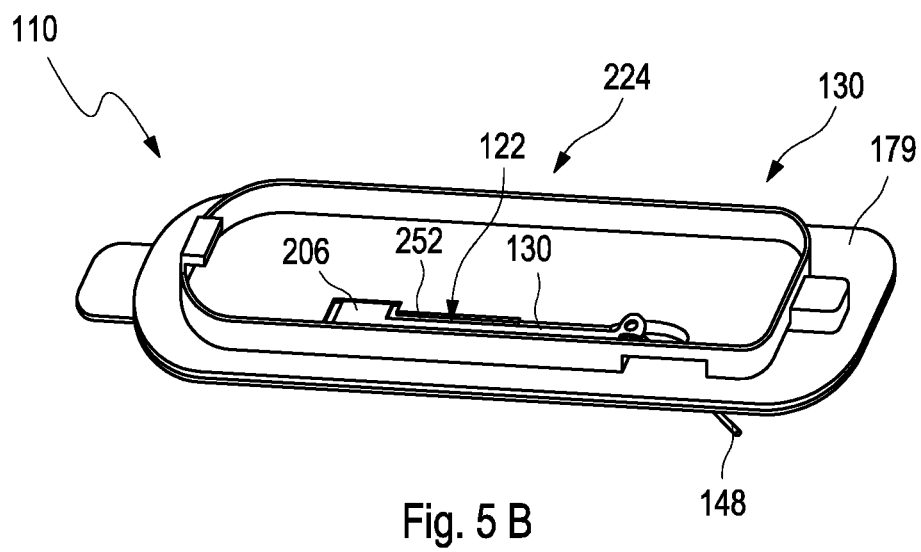

FIG. 5A and FIG. 5B show an exemplary further embodiment of a medical device 110 in a perspective view. The medical device 110 is depicted without the electronics unit 172. The medical device 110 comprises the analyte sensor 122 with the insertable portion 160 and the insertion cannula 114. Further, the medical device 110 may comprise the housing 130 with the adhesive element 179. The medical device 110 may correspond at least in large parts to the medical device 110 as illustrated in FIGS. 1K to 4C. Thus, reference may be made to the description of FIGS. 1K to 4C above.

Firstly, as depicted in FIG. 5A, the insertion cannula 114 may be in the retracted position 222. The connector portion 206 may be fixedly attached to the housing 130. The active portion 148 may be received in the insertion cannula 114 and the passive portion 152 may at least partially form the reserve loop 150. The reserve loop 150 may have a basic shape which corresponds to an elliptical shape. The reserve loop 150 may extend along a direction 248 transverse to a direction of extension 250 of the housing 130.

Further, as depicted in FIG. 5B, when the insertion cannula 114 may be in the extended position 224, the insertable portion 160 may be received in the body tissue (not shown) and the passive portion 152 may at least partially lie flatly within a receptacle 252 of the housing 130.

Figure 6:
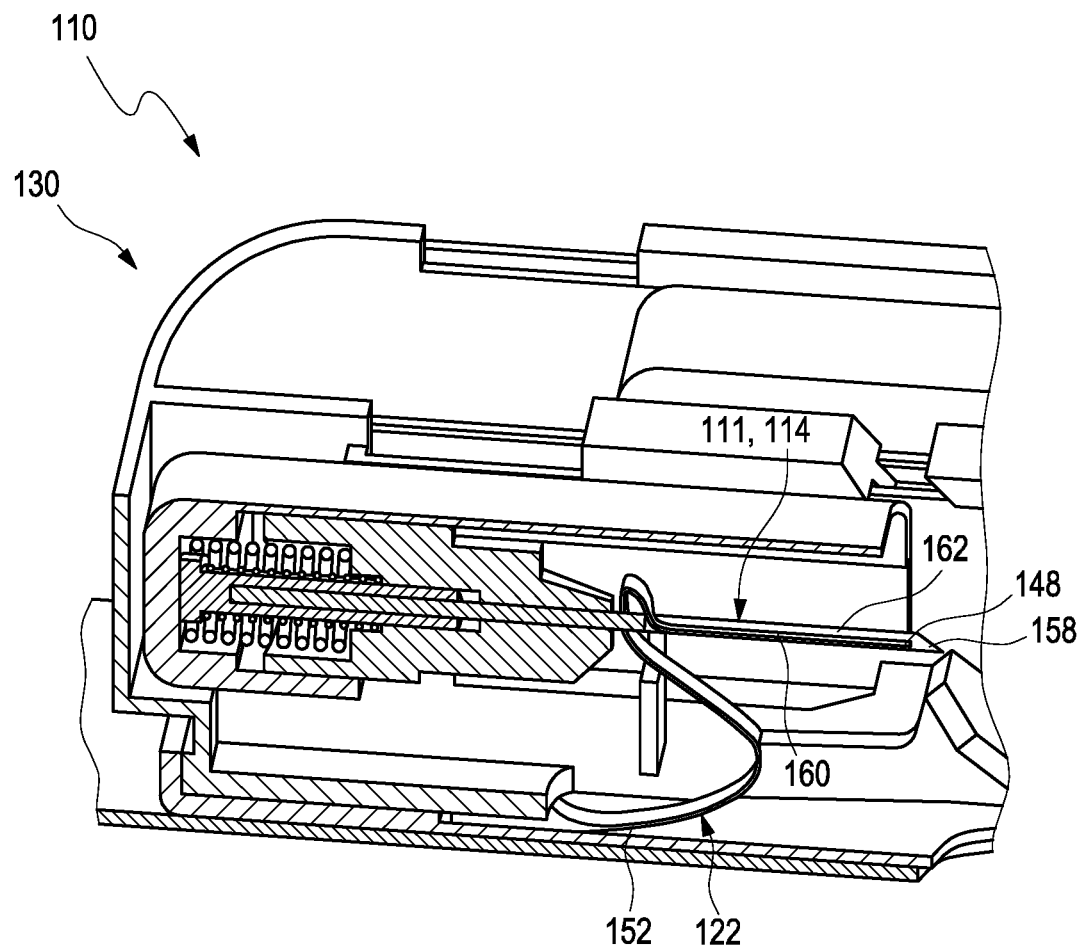
FIG. 6 show a section of an exemplary further embodiment of a medical device in a cross-sectional view.

FIG. 6 shows a section of an exemplary further embodiment of a medical device 110 in a cross-sectional view. The medical device 110 corresponds at least in large parts to the medical device 110 as depicted in FIGS. 1K to 5B. Thus, reference may be made to the description of FIGS. 1K to 5B above.

The medical device 110 may comprise the insertion cannula compartment 132. The insertable portion 160 of the analyte sensor 122 may be received within the insertion cannula 114. the passive portion 152 may at least partially form the reserve loop 150. The reserve loop 150 may have a basic shape which corresponds to an elliptical shape. Through such a configuration a vertical insertion wherein the insertion cannula 114 is inserted within at angle of 90° to the skin site (not shown) may be feasible.

LIST OF REFERENCE NUMBERS 110 medical device
111 slotted cannula
112 intermediate product
113 slot
114 insertion cannula
115 axial direction
116 insertion cannula slider
118 part
120 housing
122 analyte sensor
124 analyte sensor slider
126 receptacle
127 biocompatible coating
128 part
130 housing
132 insertion cannula compartment
134 electronics unit compartment
136 first component
138 section
139 clamp
140 separating wall
142 further section
144 second component
146 analyte sensor receptacle
147 adhesive
148 active portion
150 reserve loop
152 passive portion
154 intermediate portion
156 insertion cannula receptacle
158 end
160 insertable portion
162 lumen
163 part
164 cover element
165 further part
166 opening
167 sealing element
168 sealing foil
169 passage opening
170 sealing film
172 electronics unit
174 interconnect device
176 printed circuit board
178 electronic component
179 adhesive element
180 bottom side
182 adhesive surface
184 cover element
186 skin site
188 insertion aid
190 insertion aid receptacle
192 button
194 body tissue
196 detachable cap
198 septum
200 opening
202 substrate
204 shaft
206 connector portion
208 sensor electrode
210 working electrode
212 reference electrode
214 counter electrode
216 electrical contact
218 electrical trace
220 part
222 retracted position
223 folded section
224 extended position
226 reserve loop receptacle
227 major axis
228 fold-back structure
229 direction of extension
230 shaft loop
231 direction
232 first part
234 second part
236 first end
238 second end
239 first shape configuration
240 layer
241 second shape configuration
242 direction of extension
244 curved section
246 cover element receptacle
248 direction
250 direction of extension
252 receptacle

The invention claimed is:

1. A medical device for detecting at least one analyte in a body fluid, the medical device comprising:
at least one analyte sensor having an insertable portion adapted for at least partially being inserted into a body tissue of a user,
at least one electronics unit, wherein the at least one analyte sensor is operably connected to the at least one electronics unit, wherein the at least one electronics unit comprises at least one interconnect device with at least one electronic component attached thereto;
at least one insertion cannula, wherein the at least one analyte sensor is partially is placed inside the at least one insertion cannula;
wherein the at least one insertion cannula is movable in between at least one extended position and at least one retracted position, wherein the at least one electronics unit remains in a fixed position when the at least one insertion cannula is moved from the at least one extended position to the at least one retracted position or vice versa;

wherein the at least one analyte sensor comprises at least one active portion having at least one sensor electrode for sensing the analyte thereon;

wherein the at least one analyte sensor further comprises at least one passive portion electrically connected to the at least one electronics unit in at least one connector portion;

wherein the at least one passive portion provides, in between the at least one connector portion and the at least one active portion, at least one reserve loop configured for compensating for an insertion path during movement from the at least one retracted position into the at least one extended position or vice versa, wherein the medical device comprises at least one analyte sensor slider, wherein the at least one analyte sensor slider is configured to be movable within the medical device when the at least one insertion cannula is moved from the at least one retracted position to the at least one extended position, wherein the at least one analyte sensor slider comprises at least one receptacle, wherein the at least one receptacle is configured to receive the at least one reserve loop at least partially when the at least one insertion cannula is in the at least one retracted position.

2. The medical device according to claim 1, wherein the at least one reserve loop comprises at least one folded section of the at least one analyte sensor.

3. The medical device according to claim 1, wherein the at least one reserve loop has a radius of less than 10 mm.

4. The medical device according to claim 1, wherein the at least one reserve loop has a basic shape that corresponds at least partially to a form selected from the group consisting of: a circular shape, an oval shape, an elliptical shape, a meandering shape, a curved shape, a bent shape, a kinked shape, a folded shape, a leporello fold shape, and a spiral shape.

5. The medical device according to claim 1, wherein the at least one analyte sensor is stored in a first shape configuration when the at least one insertion cannula is in the at least one retracted position, wherein the at least one analyte sensor is configured to be transformable into a second shape configuration when the at least one insertion cannula is in the at least one extended position.

6. The medical device according to claim 1, wherein the at least one reserve loop is formed according to one of the following options:

the at least one reserve loop is formed or magnified when the at least one insertion cannula is in the at least one retracted position, wherein the at least one reserve loop is configured to be completely or at least to a large extend diminished when the at least one insertion cannula is in the at least one extended position; or the at least one reserve loop is formed when the at least one insertion cannula is in the at least one extended position, wherein the at least one reserve loop is configured to be completely or at least to a large extend diminished when the at least one insertion cannula is in the at least one retracted position.

7. The medical device according to claim 1, wherein the at least one insertion cannula is selected from the group consisting of: a closed cannula with the wall circumferentially enclosing a lumen of the insertion cannula; and a slotted cannula, with the insertion cannula having a slot extending in an axial direction.

8. The medical device according to claim 1, wherein one part of the at least one analyte sensor is received in the at least one insertion cannula, wherein one further part of the at least one analyte sensor is located outside of the at least one insertion cannula.

9. The medical device according to claim 8, wherein the at least one analyte sensor is folded such that the further part of the at least one analyte sensor is located adjacent to the at least one insertion cannula.

10. The medical device according to claim 1, wherein the medical device comprises at least one housing, wherein the at least one housing comprises at least one electronics unit compartment and at least one insertion cannula compartment, wherein the at least one electronics unit is at least to a large extend received in the at least one electronics unit compartment, wherein the at least one insertion cannula is at least to a large extend received in the at least one insertion cannula compartment when the at least one insertion cannula is in the at least one retracted position.

11. The medical device according to claim 10, wherein the at least one insertion cannula compartment and the at least one electronics unit compartment are separated by at least one separating wall, wherein the at least one separating wall comprises at least one analyte sensor receptacle, wherein an intermediate portion of the at least one analyte sensor is received in the at least one analyte sensor receptacle.

12. A method of using the medical device of claim 1, wherein the method comprises:

placing the medical device onto a skin site of the user, with the at least one insertion cannula being in the at least one retracted position;

extending the at least one insertion cannula into the at least one extended position, whereby a shape of the at least one reserve loop is altered as the active portion advances into the body tissue; and retracting the at least one insertion cannula into the at least one retracted position, with the active portion remaining in the body tissue.

13. The method according to claim 12, wherein the altering of the shape of the at least one reserve loop comprises at least one selected from the group consisting of: a diminishing of the at least one reserve loop, a magnifying of the at least one reserve loop, and a forming of the at least one reserve loop.

14. A method of assembling the medical device of claim 1, wherein the method comprises:

providing a housing of the medical device, the housing comprising at least one insertion cannula compartment and at least one electronics unit compartment;

placing the at least one analyte sensor into the housing, wherein the at least one active portion and the at least one reserve loop are at least partially placed in the at least one insertion cannula compartment and the at least one connector portion is at least partially placed in the at least one electronics unit compartment;

sterilizing the at least one insertion cannula compartment; and electrically connecting the at least one electronics unit to the at least one passive portion of the at least one analyte sensor.

* * * * *